United States Patent [19]

Knight et al.

[11] Patent Number: 5,741,521
[45] Date of Patent: Apr. 21, 1998

[54] BIODEGRADABLE CONTROLLED RELEASE AMYLACEOUS MATERIAL MATRIX

[75] Inventors: Adrian Timothy Knight, Lane Cove; Thomas Peter Anderson, Manly West; Mirsad Ahmet Ahmetagic, Albany Creek, all of Australia

[73] Assignees: Goodman Fielder Limited; Incitec Limited, both of Australia

[21] Appl. No.: 454,093

[22] Filed: May 30, 1995

Related U.S. Application Data

[63] Continuation-in-part of Ser. No. 838,802, May 11, 1992, abandoned.

[30] Foreign Application Priority Data

Sep. 15, 1989 [AU] Australia .................. PJ 6411

[51] Int. Cl.⁶ .......................... A01N 25/10; A01N 25/14; A01N 25/34; B29C 47/00
[52] U.S. Cl. .............. 424/488; 424/486; 424/487; 424/409; 424/499; 424/501; 424/195.1; 71/64.01; 71/64.03; 71/64.07; 71/DIG. 1; 264/176.1; 264/186; 264/184; 264/211
[58] Field of Search ..................... 424/486, 488, 424/487, 499, 501, 409; 71/64.01, 64.03, 64.07, DIG. 1

[56] References Cited

FOREIGN PATENT DOCUMENTS 2887689  8/1989  Australia .
2227245  7/1990  United Kingdom .

Primary Examiner—Edward J. Webman

[57] ABSTRACT

A biodegradable or digestible matrix is provided suitable for use as a controlled release of an agriculturally active agent such as insecticides, fungicides, fertilizers, plant growth regulants, etc. The matrix comprises an amylaceous material optionally in association with a synthetic polymer and is formed under elevated temperature and pressure.

49 Claims, 34 Drawing Sheets

BIODEGRADABLE CONTROLLED RELEASE AMYLACEOUS MATERIAL MATRIX

CROSS-REFERENCE TO RELATED APPLICATIONS

This application is a continuation-in-part application of Ser. No. 07/838,802, filed May 11, 1992, now abandoned.

TECHNICAL FIELD

This invention relates to a biodegradable or digestible matrix, and more particularly to a matrix suitable for controlled release of an active agent into an environment or for controlled rate of biodegradation or digestion. The invention also relates to a method for manufacture of the matrix and to use of the matrix in agriculture.

BACKGROUND ART

In agriculture it is desirable to release fertilizers, pesticides, herbicides or the like active agents to the soil at a controlled rate over a prolonged period. Depending on the type of active agent and the agricultural requirement, the period of release may be desirably a period of weeks, months or years. Furthermore, it is sometimes desirable that the active agent be released at an initially high rate and then at a slower rate.

It has been practised to prepare copolymers comprising a synthetic polymer as the major component with minor amounts of starch as absorbents. These grafted polymers are used in agriculture for example, as a coating for seeds. The polymer absorbs water and holds it at the seed surface, thus increasing both the rate of germination and the percentage of the total number of planted seeds which germinate. Examples include starch polyacrylates, starch acrylonitriles, starch polyethylenes, starch-vinyl copolymers and the like.

Similarly, it is known to manufacture so called biodegradable films from synthetic polymers for use in for example agriculture as mulch films. Some of these films include starch as a minor component.

However, in general, the starch-synthetic copolymer compositions and synthetic films suffer from the disadvantage that they are not truly biodegradable. Disadvantageously, when the composition disintegrates, the synthetic organic residue remains as an environmental pollutant.

It has also be practised to encapsulate active agents so that an inner core of the toxic agent is surrounded by a polymeric matrix. The polymeric matrix may include starch. These products form a sponge like structure which holds the active ingredient when dry but releases it upon wetting. Release is generally effected by the rupture of the enveloping membrane. Accordingly, although these materials may be fully biodegradable, it is difficult to control the rate of release and also to control the rate of degradation. The production of such incorporated agents involves complex and critical manufacturing steps.

The present invention stems from the surprising and unexpected discovery that an active ingredient can be controllably released into an environment at a predetermined rate from a biodegradable matrix based on a starch derived material and that the release rate of the active ingredient can be varied independently of the rate of degradation of the matrix.

The biodegradable matrix of the invention has been developed primarily for use in agriculture and will be described hereinafter with reference to that application. However, it will be appreciated that the invention is not limited to that particular field of use.

DISCLOSURE OF THE INVENTION

It is a first object of the present invention to provide a method for the manufacture of a biodegradable matrix shape having an active agent incorporated therewith to be controllably released from the matrix into an environment at a predetermined rate.

It is a second object of the present invention to provide a biodegradable composition for the controlled release of an active ingredient into an environment which in preferred embodiments, avoids or at least ameliorates the above discussed deficiencies of the prior art.

According to one aspect, the invention consists in a method for manufacture of a controlled release biodegradable matrix shape containing an agriculturally active agent subject to controlled release, said method comprising the steps of:

a) heating at a temperature of no more than about 150° C. and subjecting to a pressure of no more than about 4000 psi a composition having a water content of from about 2 to about 30% w/w and comprising an amylaceous material having an amylose content of at least 50% w/w or a derivative thereof selected or derived from the group consisting of amylose, maize starch including waxy maize starch, wheat starch, tapioca starch, pea starch or a combination thereof, and water; so as to provide a uniform hot melt without destructurising the amylaceous material or derivative thereof, b) forming the hot melt into a desired matrix shape, step (a) or step (b) further comprising including a filler in an amount of less than about 95% by weight, 0 to less than or equal to about 90% by weight of a synthetic polymer and optionally a plasticizer, if synthetic polymer is present, in an amount of about 20% by weight or less, and c) incorporating the agent in the matrix shape, the composition and forming conditions of the matrix shape being selected so as to provide a predetermined rate of biodegradation whilst the concentration and type of filler is selected so as to provide a controlled rate of release of said agent independent of said rate of biodegradation.

According to a second aspect, the invention consists in a controlled release biodegradable composition comprising a matrix formed by heating at a temperature of no more than about 150° C. and subjecting to a pressure of no more than about 4000 psi, a composition having a water content of from about 2 to about 30% w/w and comprising an amylaceous material having an amylose content of at least 50% w/w or a derivative thereof selected or derived from the group consisting of amylose, maize starch including waxy maize starch, wheat starch, tapioca starch, pea starch or a combination thereof, and water; to provide a uniform melt without destructorising the amylaceous material or derivative thereof; from 0 to less than or equal to about 25% by weight of a synthetic polymer; an active agent subject to controlled release and selected from the group consisting of acaricides, insecticides, nematicides, herbicides, fungicides, plant growth regulants, fertilizers, trace nutrients, biological control agents or a combination thereof; from 0 to about 20% w/w of plasticizer if synthetic polymer is present and a filler in an amount of less than about 95% by weight, the composition and forming conditions of the matrix being selected so as to provide a predetermined rate of biodegradation whilst the concentration and type of filler is selected so as to provide a controlled rate of release of said agent independent of said rate of biodegradation.

According to a third aspect, the invention consists in a method of agriculture which comprises applying to a crop growing area a matrix shape produced by the method according to the first aspect or the composition according to the second aspect.

For the purposes of this specification, the term "amylaceous material" means starch or flour from any cereal crop, root crop, leguminous crop or any other commercial source of starch and includes for example wheat starch, maize starch including waxy maize starch, potato starch, tapioca starch, pea starch or a combination thereof, amylose or amylopectin alone or any combination of amylose and amylopectin.

A "derivative" of amylaceous material includes modified amylaceous materials (for example chemically modified amylaceous materials), amylaceous compositions formed during hot melting or during forming amylaceous material alone or in combination with plasticizers, crosslinking agents or the like. The term also includes starch molecules having a synthetic polymer grafted thereon.

"Synthetic polymer" includes non-naturally occurring polymers such as those used for plastics and elastomers and the term includes within its scope both thermoplastic and thermosetting polymers.

The term "forming" in relation to the hot melt includes the formation of films, rods, strands, sheets, pellets or the like and includes, as the context admits, extrusion through a die head and in a blow moulding machine.

The present invention particularly relates to the controlled release of an active agent selected from the group comprising acaricides, insecticides, nematicides, herbicides, fungicides, plant growth regulants, fertilizers, trace nutrients or a combination thereof into an environment. Preferably the environment is a terrestrial environment and in a highly preferred embodiment the environment is a crop growing area. However, the invention will be understood to be suitable for use in aquatic environments.

BRIEF DESCRIPTION OF DRAWINGS

The file of this patent contains at least one drawing executed in color. Copies of this patent with color drawings will be provided by the Patent and Trademark Office upon request and payment of the necessary fee.

Preferred embodiments of the invention will now be described, by way of example only, with reference to the accompanying graphs wherein cumulative % weight loss is shown on the y axis, time of incorporation in soil (days) is shown on the x axis, soil temperature is shown in degrees Celsius and soil moisture represented by the symbols FP, H, M and L wherein FP represents a flood plot where excess water is present, H represents a high soil moisture content of from 26% to 40% by weight, M represents a medium soil moisture content of from 6% to 20% by weight and L represents a low moisture content of from 3% to 17.6% by weight.

BEST MODES FOR CARRYING OUT INVENTION

Figure 1:
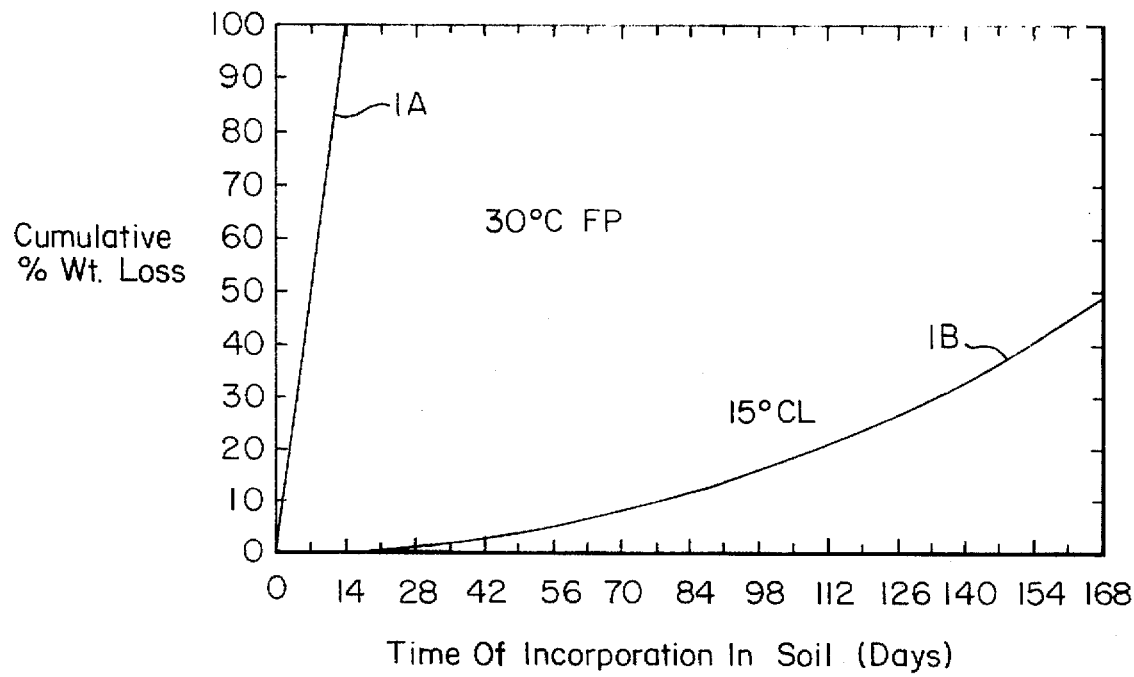
FIGS. 1 to 4 show the effect of soil moisture and soil temperature on the degradation rate of a biodegradable matrix according to the invention.

The biodegradable composition according to the invention is desirably formed from a "hot melt" process.

In preferred embodiments of the method for manufacture according to the invention, a composition comprising an amylaceous material or a derivative thereof is first prepared by mixing an amylaceous material and an amount of water in sufficient proportion to form a free-flowing powder.

In preferred embodiments of the invention, the amylaceous material used is high amylose maize starch comprising at least 50% by weight of amylose or a modified derivative of this starch.

Where a high amylose maize starch is used, it is desirable to select a high amylose maize starch or modified starch derived from the Goodman Fielder Mills Pty Ltd maize hybrids 55/77 or 65/88 described in detail in the applicant's co-pending application No. PCT/AU90/00237 incorporated herein by cross-reference.

By modifying the basic starch, it is possible to confer different properties on the final matrix shape. A large number of derivatives of amylaceous materials are suitable for use in the present invention. These include (i) ether derivatives such as
   a) hydroxyalkyl derivatives, for example hydroxyethyl, hydroxypropyl and hydroxybutyl and
   b) carboxyalkyl derivatives, for example carboxymethyl, and ii) ester derivatives such as saturated fatty acid derivatives, for example acetyl and succenyl. Mixed derivatives are also suitable for use in the present invention.

In addition, the ether and ester derivatives may be crosslinked such as for example, distarch phosphate or distarch glycerol. In such case, modification may be achieved by using a crosslinking agent such as sodium trimetaphosphate. Cross bonded high amylose maize starch and cross bonded common wheat starch are particularly suitable modifications for use in the present invention. The amylaceous material may be precrosslinked, that is be crosslinked prior to or during conversion to the hot melt. However, preferably, the amylaceous material is crosslinked during forming and more preferably after forming by any suitable method readily understood by those skilled in the art. For example, in one embodiment the matrix shape is extruded into a bath comprising the crosslinking agent, saturation allowed to take place and the matrix removed and allowed to dry and cure.

Derivatives which confer various degrees of hydrophobicity to the finished composition are particularly desirable. Such derivatives include amylaceous alkylsuccinates and in particular, starch octenyl succinate and starch molecules having synthetic polymeric branches grafted thereon. However, carboxymethylated, hydroxypropylated and acetylated high amylose modified maize starch derivatives are preferred.

By selecting the starch modification, the mechanical properties of the matrix shape may be varied. For example, the selection of an acetylated high amylose starch having an acetyl value of about 2.5% or a hydroxypropylated high amylose starch having a hydroxypropyl value of up to about 3% allows higher processing temperatures to be utilized thereby resulting in films having improved handling characteristics in that the hot melt is less fluid and more rubbery in nature. Carboxymethylated starch derivatives having a carboxyl value of about 2% are also particularly suitable for use in the present invention.

The nature of the crosslinking agent and the stage at which the crosslinking agent is incorporated into the amylaceous material affects such physical properties of the matrix shape as biodegradability, release rate, flexibility, strength, surface finish and colour.

For a uniform hot melt phase to form, it is believed necessary that an amount of water be present in the composition used to form the hot melt. Preferably, the composition contains water in less than the minimum amount required to dissolve all the amylaceous solid material, that is the composition contains less than about 50% by weight of water. More preferably, the composition comprises from about 2% to about 30% by weight of water. However, the minimum amount of water required to form a uniform hot melt may be employed. Accordingly, the amount of water may vary down to a few percent. It is emphasised that these amounts represent the total amount of water in the composition used to form the hot melt and not the amount of added water. In fact, amylaceous material as normally dried in preparation typically comprises from 9 to 20% by weight of water and as such, the residual moisture inherent in the amylaceous material may be sufficient to enable the conversion of the composition into a hot melt and additional water need not be added or be added in small quantities only. However, preferably, water is added in an amount of less than 50% by weight, more preferably less than 20% by weight and most preferably from about 5% to about 15% by weight.

The amount of water may be selected so as to modify the physical properties of the final product. For example, the higher the water content, the higher the flexibility and the lower the strand strength of the matrix shape.

In addition to the amylaceous material and water, the composition for preparing the hot melt may also include optional ingredients such as synthetic polymers, fillers, plasticizers, weighting agents, U.V. stabilizers, pore structure modifiers and the like.

The applicant has discovered that the addition of synthetic polymers during the preparation of the biodegradable matrix shape affects both the performance and processing of the matrix. Preferably, the synthetic polymer is added to the composition before processing to a hot melt, although it may be added during the conversion or be applied to the matrix shape itself during forming by way of co-forming or alternatively, the matrix shape may be coated immediately after forming, for example by way of spraying, brushing or dipping. The co-forming technique employed may be any one of those currently used in the plastic industry, for example thermal lamination, co-injection or co-extrusion using the cast (flat die) method or strand die method or in blown film production.

The applicant has discovered that the inclusion of a synthetic polymer in the biodegradable matrix shape results in a more absorbent product for some active agents and a matrix shape having a greater shelf life stability. Further, the applicant has made the surprising and unexpected discovery that where an ethylene vinyl acetate starch copolymer is used, a two phase system forms in the cooled matrix. The presence of these two apparently continuous phases of starch and synthetic polymer results in a very high surface area honeycomb of the ethylene vinyl acetate phase once the starch phase has degraded. Further, the phase separation/compatibility may be adjusted by modifying the side chain components of the modified starches.

The synthetic polymer may be added in an amount of up to about 90% by weight of the composition, hot melt or the matrix shape respectively. However, preferably, no more than about 25% by weight and more preferably less than or equal to about 15% by weight synthetic polymer is added since in general, the larger the synthetic polymer component, the slower the degradation rate of the matrix shape.

The synthetic polymer may be any conventional thermoplastic or thermosetting polymer but is preferably selected from the group consisting of polyethylene (including low density polyethylene, linear low density polyethylene and high density polyethylene), ethylene vinyl acetate copolymers, ethylene acrylic acid copolymers, polyvinyl chlorides, polystyrenes, chlorinated polyethylenes, ethylene propylene copolymers, acrylic acid copolymers, polyvinyl acetals copolymers, polyamines, polyethylene terephthalates, phenolic resins and urethanes. Most preferably, the synthetic polymer is thermoplastic and is low density polyethylene, linear low density polyethylene, or high density polyethylene; an ethylene vinyl acetate copolymer having a vinyl acetate content of from 5% to 40% W/W and melt flow index of from 0.5 to 400 g/10 minute as determined by the ASTM test D1238; or polyvinyl chloride or chlorinated polyethylene having a chlorine content of from 20% to 50% W/W.

The synthetic polymer may be selected to modify or decrease both the biodegradation rate of the matrix shape and the release rate of the active agent. Further, the applicant has found that the addition of a synthetic polymer to the matrix affects the mechanical properties of the finished article. For instance, at the 10% addition level both chlorinated polyethylene and polyvinyl chloride increase strand strength and flexibility of the final matrix shape. Conversely, at the 10% addition level, ethylene vinyl acetate copolymers decrease strand strength yet increase flexibility. Both strand strength and flexibility are advantageous for the purposes of handling and storage of the finished product as matrices exhibiting these properties tend to retain their shape and integrity.

The addition of non polymeric fillers also serves to modify processing and performance characteristics of the hot melt and final product. Fillers may be added to the composition prior to conversion into the hot melt or be added to the hot melt prior to formation of the matrix shape. Water soluble, water insoluble, organic, inorganic, ionic and non-ionic fillers are suitable for use in the present invention. Preferably, the selected filler is non-toxic to the environment. Specific examples of suitable fillers include metal salts, clays, carbonaceous materials, dextrose, talc, silicas and ammonium sulphate. Preferably, the metal salt is calcium carbonate, calcium sulphate, sodium carbonate, sodium sulphate or barium sulphate, the clay kaolin or bentonite and the carbonaceous material wood flour. The fillers may be included in the formulation at levels up to about 70% by weight. However, formulations comprising up to about 95% by weight non polymeric filler are also envisaged by the present invention.

The addition of plasticizers and lubricants improves both the extrusion characteristics of the hot melt and the physical properties of the matrix shape. The plasticizer may be added to the composition prior to conversion into the hot melt or to the hot melt prior to formation. Generally, any known plasticizer can be utilized in the present invention. However, specific examples of suitable plasticizers include mono or polyfunctional alcohols. Polyethylene glycol, acetyl glycol, glycerol, invert sugar, dioctyl phthalate, vegetable oils (preferably soya bean oil), chlorinated hydrocarbons and combinations thereof are preferred.

The amount of plasticizer to be used will vary up to about 20% by weight of the formulation. However, the presence of an auxiliary plasticizer is not essential.

In order for the hot melt to form, the amylaceous containing composition must be subjected to elevated temperatures and pressure. The temperatures best suited for this conversion are from about 70° C. to about 150° C. depending on the formulation. Where the matrix shape is formed without vacuum venting in an extruder, the preferred temperatures are as set out below.

vacuum stripping step at a pressure of for example less than 200 mbar. Alternatively, the hot melt is subjected to a series of reduced pressures prior to the forming step to sequentially remove a potion of the water and other volatiles from the hot melt at each venting step.

The hot melt is then formed into the desired matrix shape by any conventional process such as dies or rolls into any desired size or shape including pellets, chips, ribbons, films and the like.

In another embodiment of the invention, the matrix obtained from the process described hitherto and an amount of water sufficient to form a uniform hot melt is subsequently subjected to elevated temperatures and pressures for conversion into a second hot melt which can be shaped or moulded by any conventional process into the desired shape and size as described above.

If desired, some or all of the optional ingredients such as synthetic polymers, fillers, plasticizers and the like hitherto described may be added before, during or after this second processing step in accordance with the teachings set forth above.

| EXTRUDER | WITHOUT SYNTHETIC POLYMER Temperature (°C.) | WITH SYNTHETIC POLYMER Underwater pelletising Temperature(°C.) | Strand Pelletising |
|---|---|---|---|
| Zone - 1 | 70–80 | 120–135 | 120–135 |
| 2 | 70–80 | 120–135 | 130–135 |
| 3 | 70–85 | 125–135 | 130–135 |
| 4 | 75–85 | 130–138 | 135–140 |
| 5 | 80–85 | 130–140 | 135–140 |
| 6 | 85–90 | 130–140 | 135–140 |
| Melt Pump | | | |
| Zone - 7 | 85–90 | 130–140 | — |
| 8 | 85–90 | 130–140 | — |
| 9 | 85–90 | 130–140 | — |
| Melt Filtration | | | |
| Zone 10 | 85–90 | 130–140 | — |
| 11 | 85–90 | 130–140 | — |
| 12 | 85–90 | 130–140 | — |
| Die Transition | 85–95 | 130–140 | — |
| Die Plate | 85–95 | 130–140 | 140–145 |

However, where the active agent has been incorporated before or during processing, the conversion and forming steps respectively are preferably performed below the temperature at which the active agent breaks down. Where the active agent is incorporated with the matrix shape after forming, higher processing temperatures may be used providing the matrix shape is cooled or allowed to cool prior to incorporating the active agent therewith.

The pressure for conversion of the amylaceous containing composition to a hot melt is about 200 psi to about 4000 psi, preferably as set out below.

The active agent may be added in powder or liquid form as part of the formulation before conversion to either the first or second hot melt, during either conversion or be incorporated with either the first or second matrix shape during or after forming for example, by way of immersion or infusion. Preferably, the active agent is incorporated during the final forming step when the active ingredient may be intimately mixed with the hot melt.

The active agent is preferably selected from the group comprising acaricides, insecticides, nematicides, herbicides, trace nutrients, plant growth regulants, fertilizers,

| | WITHOUT SYNTHETIC POLYMER PRESSURE (psi) | WITH SYNTHETIC POLYMER PRESSURE (psi) Underwater pelletising | Strand Pelletising |
|---|---|---|---|
| EXTRUDER | 200–500 | 1000–2000 | 100–1000 |
| MELT PUMP OUTLET | 1500–2500 | 1500–2500 | — |
| DIE TRANSITION | 1500–2500 | 1500–2000 | — |

In one embodiment, the hot melt is subjected to a reduced pressure immediately prior to the forming step to remove water and other volatiles from the hot melt. This step is especially desirable where the melt is to be extruded as a film. Desirably, the reduced pressure is in the form of a fungicides, microorganisms for biological control or the like, or combinations thereof.

Representative examples of acaricides, insecticides and nematicides known to those skilled in the art include the following available chemicals, expressed by common name:

cadusafos, carbofuran, carbosulfan, chlorfenvinphos, chlormephos, chlorpyrifos, chlorpyrifos-methyl, cloethocarb, cyhalothrin, deltamethrin, alphamethrin, dicrotophos, disulfoton, endosulfan, ethiofencarb, ethoprophos, fenamiphos, fensulfothion fonofos, furathiocarb, isazofos, methomyl, monocrotophos, oxamyl, parathion-methyl, parathion, phorate, pirimicarb, pirimiphos ethyl, pirimiphos methyl, quinalphos, tefluthrin, temephos, terbufos.

Herbicides to be used in the composition of the present invention depend on the plant desired to be destroyed. Therefore, the class of herbicides known to those skilled in the art for destroying undesirable plants are active agents within the concept of the present invention. Representative examples of herbicides, expressed by common name, include the following: ametryn, amitrole, atrazine, bromoxynil, chlorsulfuron, cyanazine, 2,4-D and related compounds, desmethryn, di-allate, diquat, diuron, EPTC glyphosate linuron, MCPA and derivatives, metolachlor, metribuzin, paraquat, pendimethalin, picloram, simazine, terbutryn, triallate, triclopyr, trifluralin.

Similarly, the fungicides to be used in the composition of the present invention depends upon the fungi desired to be destroyed. Representative examples of fungicides known to those skilled in the art and suitable for use in the present invention include the following expressed by common name: benalaxyl, benomyl, chlorothalonil, etridiazole, fosetyl, phosphoric acid and its salts and derivatives, imazalil, metalaxyl, pyrazophos, quintozene, triadimefon.

Specific examples of plant growth regulants, that is compounds especially formulated to make a specific portion of the plant grow faster than others, and other compounds suitable for incorporation with the matrix shape include: chlormequat, nitrapyrin, paclobutrazol, urea, monoammonium phosphate, diammonium phosphate, chelated trace elements, trace nutrients, potassium sulphate, ammonium sulphate, potassium ammonium sulphates.

Suitable trace nutrients include those compounds recognised as essential or desirable for healthy plant growth and include amongst others, oxides and salts of trace elements utilized by plants.

Suitable microorganisms for biological control include *Bacillus thuringiensis*.

The nature of the active agent may be selected on the basis of the desired release rate of the final biodegradable composition.

The biodegradable compositions according to the invention comprise a matrix including an amylaceous material or derivative thereof, from 0 to less than or equal to about 25% by weight of a synthetic polymer and an active agent intended to be released into an environment at a predetermined rate. Preferably, the matrix comprises less than or equal to about 15% by weight synthetic polymer.

Desirably, the matrix is formed from an amylaceous hot melt and more desirably, by the method described above. The amylaceous material or derivative thereof and synthetic polymer may be any one of the products already described. Additionally, the matrix may include other optional ingredients such as fillers, plasticizers, weighting agents, U.V. stabilizers, pore structure modifiers and the like, the nature of which has been discussed previously.

Preferably, the final matrix includes water in an amount of from about 1% to about 50% by weight and more preferably, from about 2% to about 30% by weight.

The biodegradable matrix shapes and compositions according to the invention are particularly suitable for use in agriculture where they are applied for example, as pellets or ribbons to a crop growing area to improve plant growth and yield over an extended period of time. The matrix shapes and compositions may be applied on top of the soil but desirably, they are applied within the soil. They may be applied to the crop growing area by any conventional means including ploughing, tilling, banding, cultivating, furrowing and the like.

The release of the active agent from the biodegradable matrix is thought to be effected by two main mechanisms, diffusion through the matrix and by leaching through pores either inherent in the matrix or induced by the leaching out of soluble salts during service. Further, as the matrix is itself degrading during service, variations in the matrix surface area exposed to the environment also affects the rate of release indirectly so the release rate of the active agent may be controlled to an extent by controlling the rate of biodegradation of the matrix.

As illustrated by the following examples, and with reference to FIGS. 1 to 16, it is possible to select both the release rate and biodegradation rate of the matrix shape by the selection of starch type, additives to be incorporated into the matrix, active agent type and processing conditions.

The formulations represented by FIGS. 1 to 16 are depicted in the following table.

TABLE 1

| % W/W OF FORMULATION | 1A | 1B | 2A | 2B | 3A | 3B | 3C | 4A | 4B | 5A | 5B | 6A | 6B | 7A | 7B | 8A | 8B | 8C |
|---|---|---|---|---|---|---|---|---|---|---|---|---|---|---|---|---|---|---|
| A877[1] | 63.0 | | 72.1 | 72.1 | | | | | | 56.6 | 56.6 | 56.6 | 56.6 | | | 72.1 | 63.0 | 31.4 |
| Gelose 50[2] | | 62.0 | | | 52.8 | 52.8 | 52.8 | 62.0 | 62.0 | | | | | | | | | |
| Gelose 22[3] | | | 64.7 | 64.7 | | | | | | | | | | | | | | |
| $H_2O$ | 15.6 | 30.0 | 16.1 | 16.1 | 25.5 | 25.5 | 25.5 | 30.0 | 30.0 | 13.5 | 9.9 | 9.9 | 9.9 | 14.4 | 14.4 | 16.1 | 15.6 | 7.8 |
| Glycerol | 11.4 | 8.0 | 11.8 | 11.8 | 6.8 | 6.8 | 6.8 | 8.0 | 8.0 | 10.8 | 10.8 | 10.8 | 10.8 | 10.6 | 10.6 | 11.8 | 11.4 | 5.7 |
| Dextrose | 10.0 | | | | | | | | | | | | | | | | | |
| Omyacarb 10[4] | | | | | | | | | | | | | | | | | | |
| $BaSO_4$ | | | | | | | | | | | | | | | | | | |
| $(NH_4)_2SO_4$ | | | | | | | | | | | | | | | | | | |
| Kaolin | | | | | | | | | | | | | | | | | | |
| EVA[5] | | | | | 14.9 | 14.9 | 14.9 | | | | | | | 10.0 | 55.1 | | | |
| Sodium Trimeta Phosphate | | | | | | | | | | | 3.6 | 3.6 | 3.6 | | | | | |
| $NaHCO_3$ | | | | | | | | | | 9.0 | 9.0 | 9.0 | 9.0 | | | | | |
| Active Agent | | | | | | | | | | | | | | | | | | |
| 1[6] | | | | | | | | | | 10.1 | 10.1 | 10.1 | 10.1 | 10.3 | 10.3 | | | |

TABLE 1-continued

| | | | | | | | | | | | | | | | | | |
|---|---|---|---|---|---|---|---|---|---|---|---|---|---|---|---|---|---|
| 2[7] | | | | | | | | | | | | | | | | | |
| 3[8] | | | | | | | | | | | | | | | | | |
| CPE[9] | | | | | | | | | | | | | | | | | |

| % W/W OF FORMULATION | 8D | 9A | 9B | 9C | 9D | 10A | 10B | 11A | 11B | 11C | 11D | 11E | 13A | 13B | 13C | 14A | 14B | 14C |
|---|---|---|---|---|---|---|---|---|---|---|---|---|---|---|---|---|---|---|
| A877[1] | 7.8 | 72.1 | 63.0 | 31.4 | 7.8 | 63.0 | 63.0 | 72.1 | 63.0 | 63.0 | 63.0 | 63.0 | 47.9 | 52.8 | 47.3 | | | |
| Gelose 50[2] | | | | | | | | | | | | | | | | | | |
| Gelose 22[3] | | | | | | | | | 64.7 | 63.8 | 64.5 | 23.1 | 25.5 | 22.8 | | | | |
| H$_2$O | 2.0 | 16.1 | 15.6 | 7.8 | 2.0 | 17.6 | 17.6 | 16.1 | 15.6 | 15.6 | 15.6 | 15.6 | 14.4 | 14.2 | 14.4 | 6.2 | 6.8 | 6.1 |
| Glycerol | 1.4 | 11.8 | 11.4 | 5.7 | 1.4 | 9.4 | 9.4 | 11.8 | 11.4 | 11.4 | 11.4 | 11.4 | 10.6 | 10.4 | 10.5 | | | |
| Dextrose | | | | | | | | | | | | | | | | | | |
| Omyacarb 10[4] | | | | | | | 10.0 | | | | | | | | | | | |
| BaSO$_4$ | | | | | 10.0 | | | | | | | | | | | | | |
| (NH$_4$)$_2$SO$_4$ | | | | | | | 10.0 | | | | | | | | | | | |
| Kaolin | | | | | | 10.0 | | 13.5 | 14.9 | 13.4 | | | | | | | | |
| EVA[5] | 88.8 | | 10.0 | 55.1 | 88.8 | | | | | | | | | | | | | |
| Sodium Trimeta Phosphate | | | | | | | | | | | | | | | | | | |
| NaHCO$_3$ | | | | | | | | | | | | | | | | | | |
| Active Agent | 9.3 | | | | | | | | | | | | | | | | | |
| 1[6] | | | | | | | | | 10.3 | | | 10.4 | | | | | | |
| 2[7] | | | | | | | | | | 11.6 | | | | | | | | |
| 3[8] | | | | | | | | | | | 10.6 | | | | | | | |
| CPE[9] | | 10.0 | 10.0 | | | | | | | | | | | | | | | |

| % W/W OF FORMULATION | 15A | 15B | 16A | 16B |
|---|---|---|---|---|
| A877[1] | | | | |
| Gelose 50[2] | 47.9 | 47.3 | | |
| Gelose 22[3] | | | 63.8 | 55.7 |
| H$_2$O | 23.1 | 22.8 | 14.2 | 13.8 |
| Glycerol | 6.2 | 6.1 | 10.4 | 10.1 |
| Dextrose | | | | |
| Omyacarb 10[4] | | | | |
| BaSO$_4$ | | | | |
| (NH$_4$)$_2$SO$_4$ | | | | 8.8 |
| Kaolin | | | | |
| EVA[5] | 13.5 | 13.4 | | |
| Sodium Trimeta Phosphate | | | | |
| NaHCO$_3$ | | | | |
| Active Agent | | | | |
| 1[6] | 9.3 | | | |
| 2[7] | | 10.4 | 11.6 | 11.6 |
| 3[8] | | | | |
| CPE[9] | | | | |

[1]A877 - Acetylated high amylose maize starch.
[2]Gelose 50 - High amylose maize starch.
[3]Gelose 22 - hydroxypropylated high amylose maize starch.
[4]Omyacarb 10 - One grade of CaCO$_3$ (filler).
[5]EVA - Ethylene vinyl acetate copolymer (20% vinyl acetate content).
[6]Chlorpyrifos.
[7]Carbosulfan.
[8]Phorate.
[9]Chlorinated Polyethylene (36% Cl Content).

All formulations in Table 1 were preblended for 10 minutes at ambient temperature in a high speed Prodex blender to form a free flowing uniform mixture. The blend was then extruded using a Betol BTS 40L twin screw, co-rotating, intermeshing extruder having six barrel segments each with separate heating and cooling supply and a die containing an additional two heating zones. The extruder screws were of constant root diameter with a constant diameter ratio of 25:1.

All formulations were cooled in air to form strands and pelletized in a rotary pelletizer (Cumberland manufacture) to form the desired size pellets in a continuous process. The formulations were extruded under the following conditions:

Screw speed: 160 rpm

Feed rate: 15 kg/hr

Extrusion temperature: 75°–90° C.

Extruder motorload: 7–12 amps

Extrusion pressure: 600–850 psi.

The initial moisture content and active agent content of each matrix was determined and the matrix sample incorporated in soil. Said samples were analysed at periodic intervals for weight loss and active agent loss.

Degradation of the samples were calculated as follows:

$$\text{Total weight loss} = 100 - \left[ \frac{\text{Dry Weight Retrieved}}{\text{Dry Weight Established}} \times 100\% \right]$$

$$= 100 - \left[ \frac{\text{(Sample weight} \times \text{Moisture Content) Retrieved}}{\text{(Sample Weight} \times \text{Moisture Content) Established}} \times 100\% \right]$$

Release rates were calculated as follows:

Release rates =

$$100 - \left[ \frac{\text{(Sample Weight} \times \text{Active Content) Retrieved}}{\text{(Sample Weight} \times \text{Active Content) Established}} \times 100\% \right]$$

FIGS. 1 to 4 show the variation in the degradation rate of typical matrix formulations as a function of soil moisture and temperature.

From the results obtained, it is evident that the release rates and biodegradation rates of the matrices according to the invention are affected by both their solubility in water and soil temperature.

Figure 2:
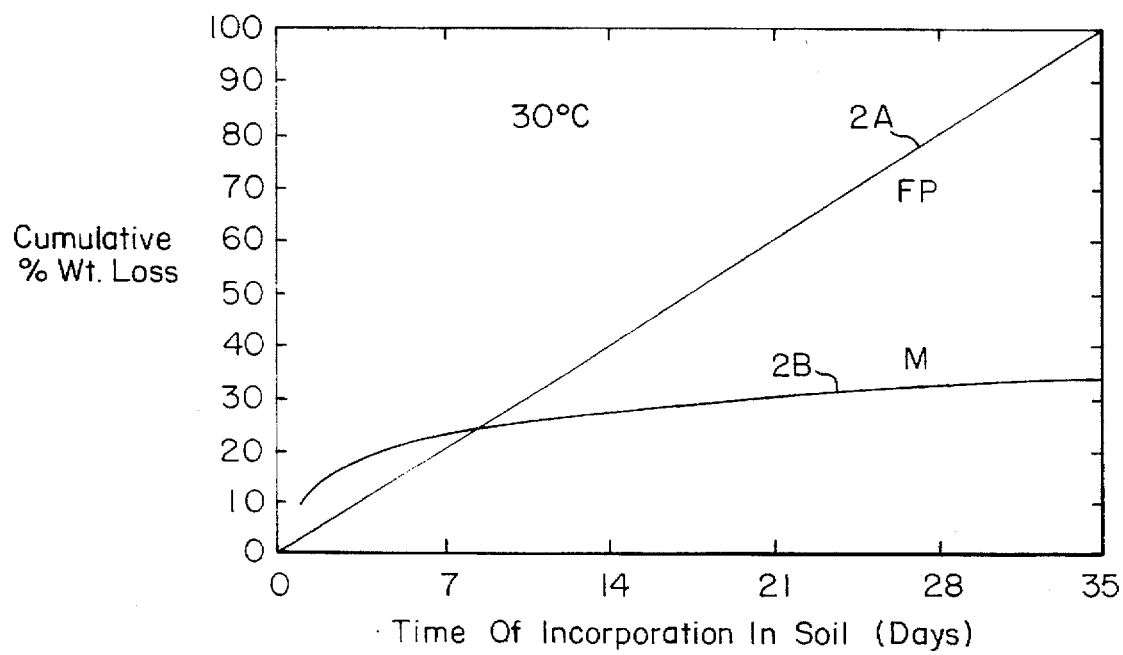
Figure 3:
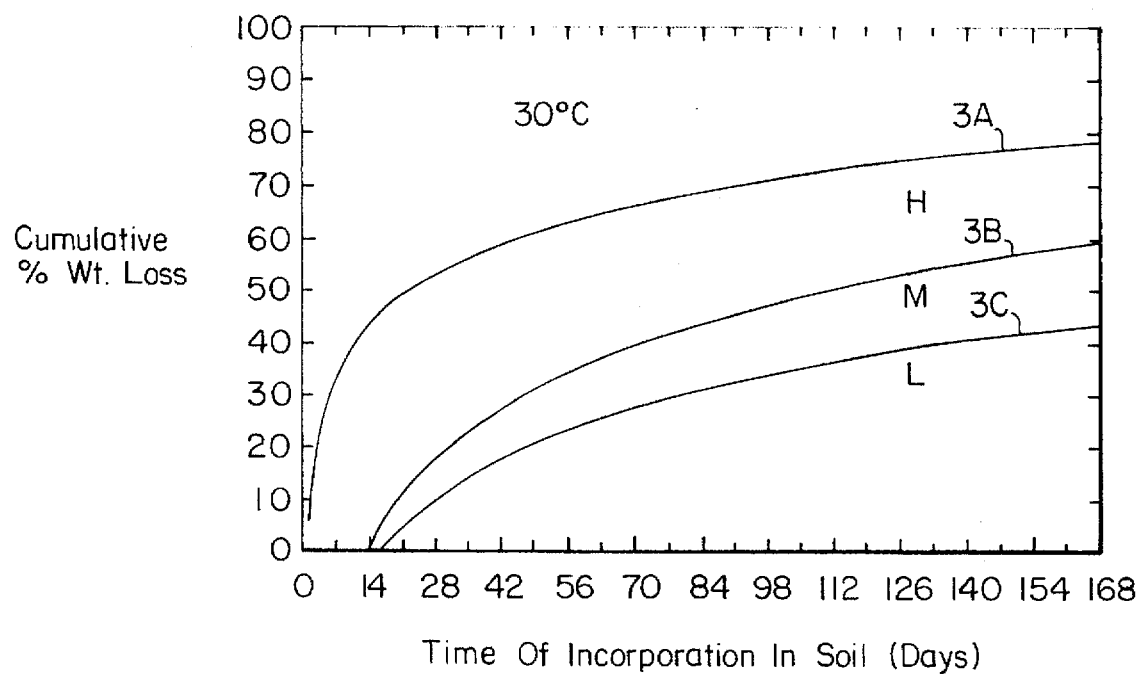
Figure 4:
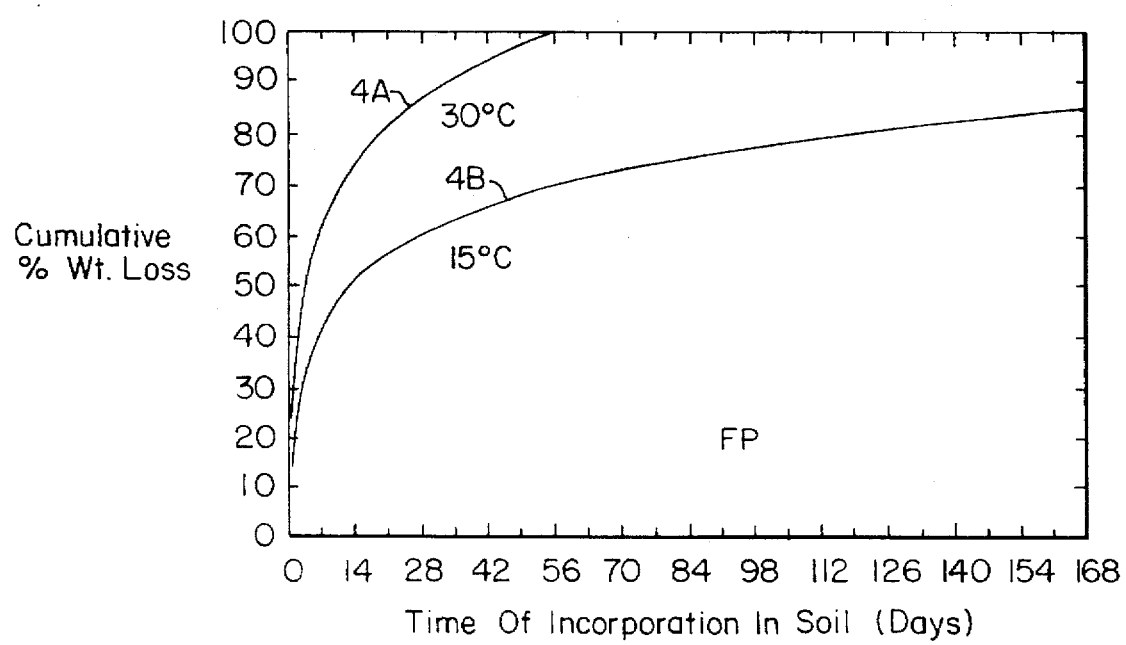

FIG. 1 shows the large difference in degradation rate and total weight loss obtainable over a period of 168 days for two formulations 1A and 1B under vastly different soil conditions, that is in a flood plot at 30° C. and a low moisture soil at 15° C. FIGS. 2 and 3 show typical degradation rates and total weight losses exhibited by a third formulation under flood plot (2A) and medium moisture conditions (2B) at a constant temperature of 30° C. over a period of 35 days. FIG. 3 compares the degradation rates and total weight losses exhibited by a fourth formulation over 168 days at 30° C. in high (3A), medium (3B) and low (3C) soil moisture conditions. FIG. 4 compares the degradation rates and total weight losses exhibited by the formulation shown in FIG. 1 as 1B at two soil temperatures [30° C. (4A) and 15° C. (4B)] but under constant soil moisture conditions. From these results it is evident that the higher the soil temperature and moisture content, the greater the amount and the faster the rate of degradation of the matrix over the specified time period.

Nevertheless, by modifying the solubility of the matrix it is possible to alter both the release rate of the active agent and the degradation rate of the matrix independently of soil conditions. For example, the release rate may be reduced by the selection of specific starch modifications which alter the hydrophobicity of the starch thereby preventing or deterring the dissolution of the starch matrices in wet environments or by modifying the starch by the introduction of active groups onto the starch chains which interact with the active agent thereby slowing down the leach out rate.

Conversely, the selection of a modified starch having reduced chain lengths induced, for example, by acid or enzyme modification, will result in a matrix exhibiting an increased rate of release.

The selection of a precrosslinked amylaceous material for subsequent conversion to the hot melt yields, after forming, a matrix shape which exhibits a relatively fast rate of release and degradation. This is somewhat surprising because crosslinked starches are typically more resistant to degradation and it is believed that this property is adversely affected by the forming step of extrusion. Conversely, where the amylaceous material is crosslinked during or after the forming step, the resulting matrix shape exhibits a slower rate of release and degradation. It is believed that this change in degradation and release rate is attributable to formation of an internally crosslinked continuous phase when the amylaceous material is crosslinked during or after forming and that this continuous phase is less susceptible to degradation. Conversely, it is thought that the use of a precrosslinked amylaceous material results in a matrix shape having a series of crosslinked phases which are more susceptible to degradation.

Figure 5:
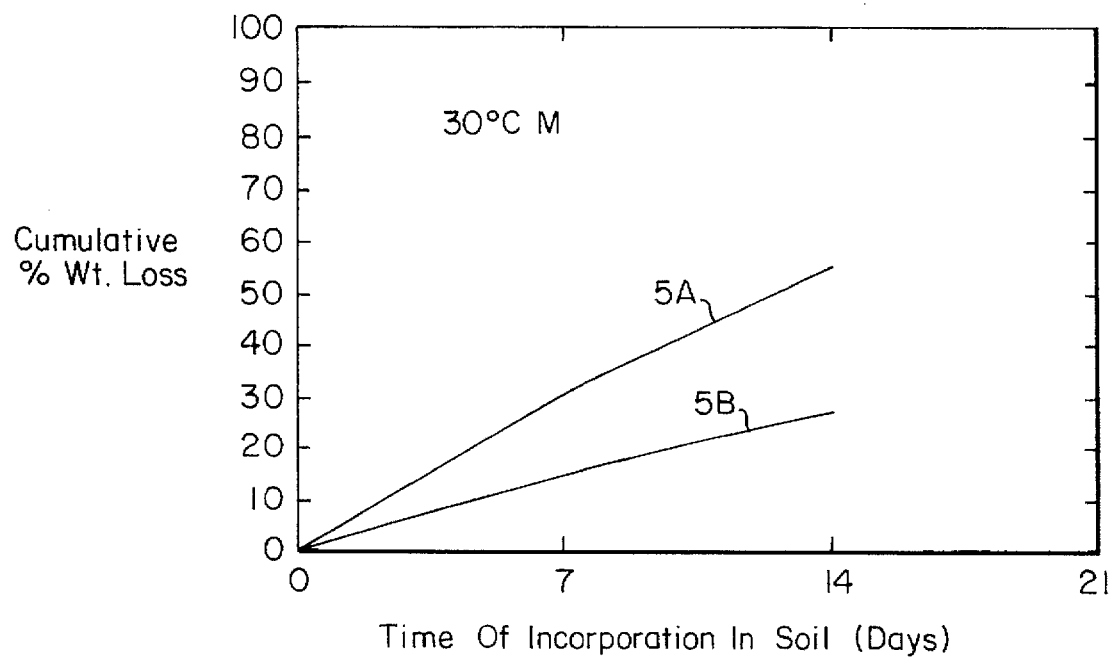
FIG. 5 shows the effect on the degradation rate of the addition of a crosslinking agent to the amylaceous material during or after forming into a matrix shape.

FIG. 5 shows the effect of crosslinking on the degradation rate and total weight loss exhibited by two matrices over a period of 14 days at a constant soil temperature (30° C.) and moisture condition (medium). The amylaceous material of matrix 5A is not crosslinked whereas the amylaceous material 5B was crosslinked after extrusion by the addition of sodium trimetaphosphate. From this Figure it is evident that the degradation rate of a matrix may be reduced by the addition of a crosslinking agent after extrusion.

The selection of certain processing conditions will also affect the properties of the amylaceous material and therefore, the release rate of the active agent. For example, by increasing the rate of shear during processing, the resulting biodegradable matrix will have shorter chains, a more degraded structure and will therefore release the incorporated active agent at a faster rate.

Figure 6:
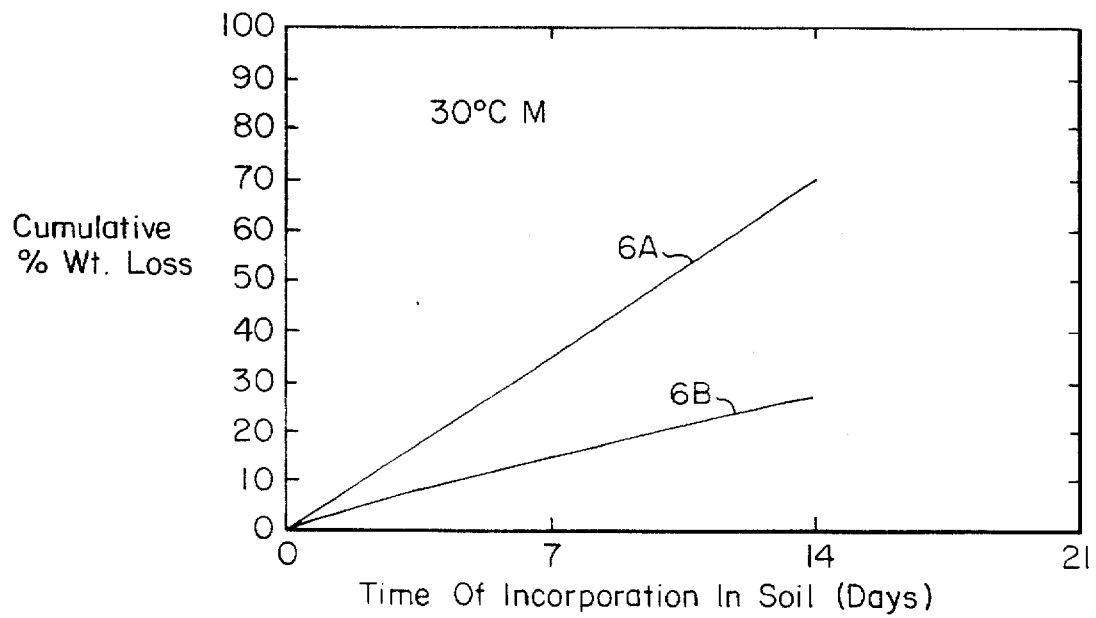
FIGS. 6 and 7 show the effect of product shape on the degradation rate of the matrix.
Figure 7:
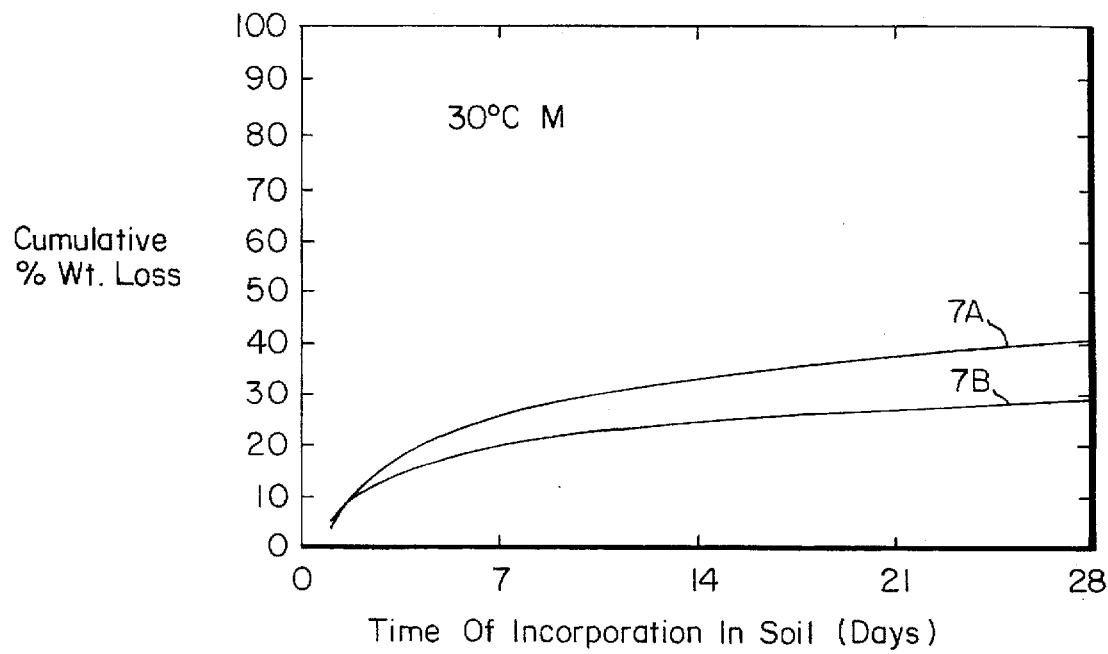

The shape of the matrix will affect its degradation rate and therefore, to an extent, the release rate of the active agent therefrom as shown by FIGS. 6 and 7 wherein matrix shapes 6A and 7A have a larger surface area than matrix shapes 6B and 7B respectively. From these Figures it is evident that the larger the surface area to volume ratio of the matrix shape, the greater the degradation rate over the specified time period.

The incorporation of a synthetic polymer with the amylaceous material or matrix shape affects both the release rate and biodegradation rate of the matrix. It is thought that the synthetic polymers affect the intermolecular voids in the matrix and thereby, the rate of diffusion and leaching out of the active agent. It is also thought that they affect the mechanical properties of the starch molecules thereby affecting the strength and solubility of the matrix shape.

Figure 8:
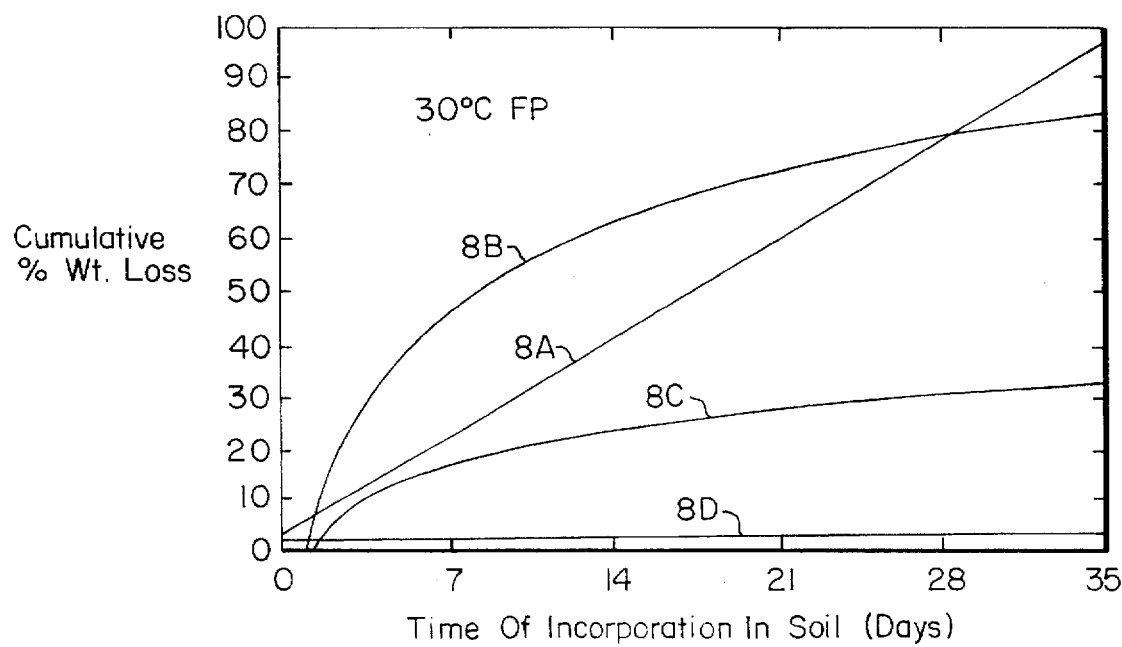
FIGS. 8 to 10 show the effect of the incorporation of synthetic polymers on the degradation rate of the matrix.
Figure 9:
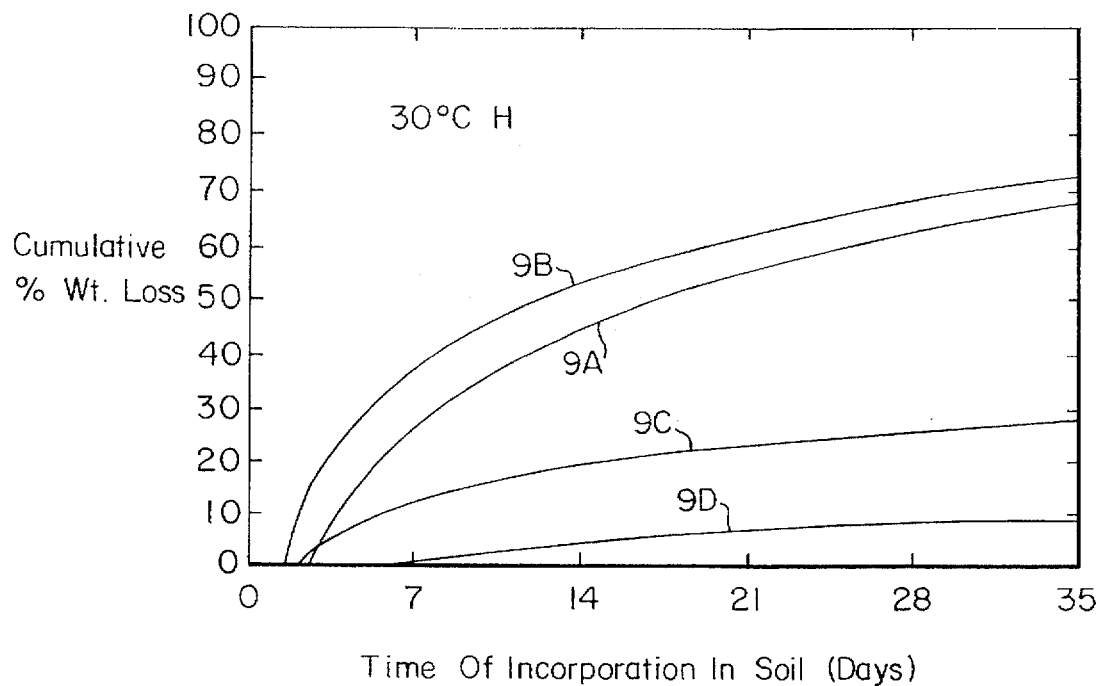

FIGS. 8 and 9 show the effect of increasing proportions of synthetic polymers on the degradation rate and total weight loss of four matrices in two soil moisture regimes, flood plot (FP) and high (H) at a constant soil temperature of 30° C. The results show little difference in the overall weight loss between the samples having 0 and 10% ethylene vinyl acetate respectively, but significant differences are apparent in both the rate of degradation and total weight loss exhibited by those matrices having higher amounts of ethylene vinyl acetate.

Figure 10:
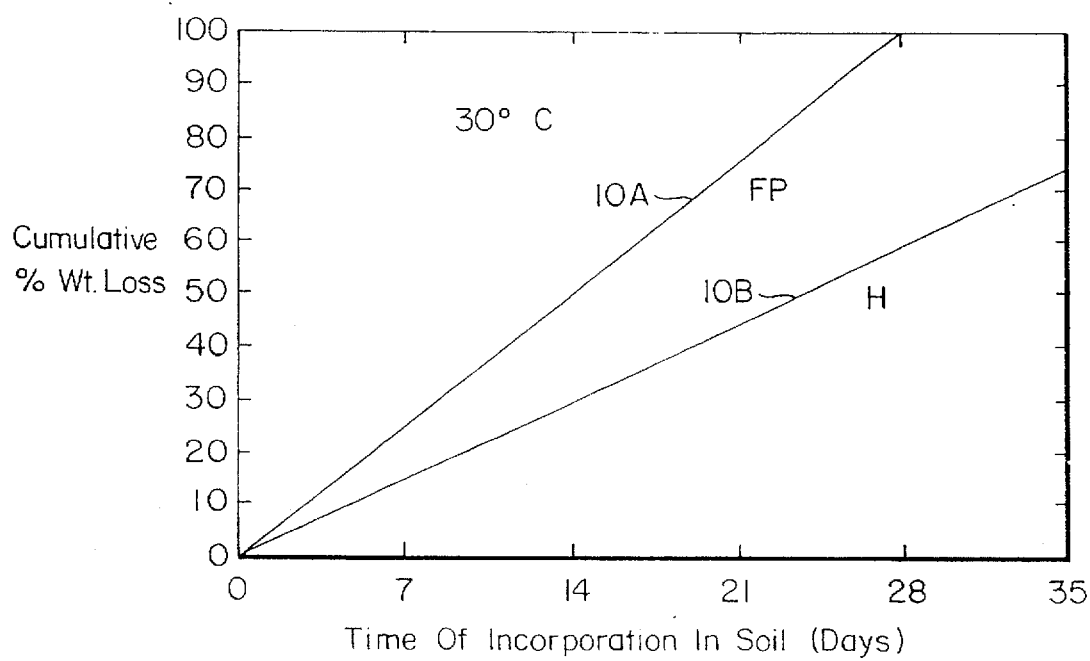

FIG. 10 shows that there is not necessarily a detectable residue from a matrix having 10% synthetic polymer (chlorinated polyethlene) incorporated therein.

The nature and amount of filler may be used to control release rates. Where a water soluble filler is incorporated with the matrix, upon contact with moisture, the filler will dissolve over time, thereby creating a series of pores through which the active agent is actually released. Conversely, the incorporation of less soluble or insoluble inert fillers with the matrix reduces the release rate as the starch and active agent is "protected" from exposure to the environment and consequent dissolution.

Figure 11:
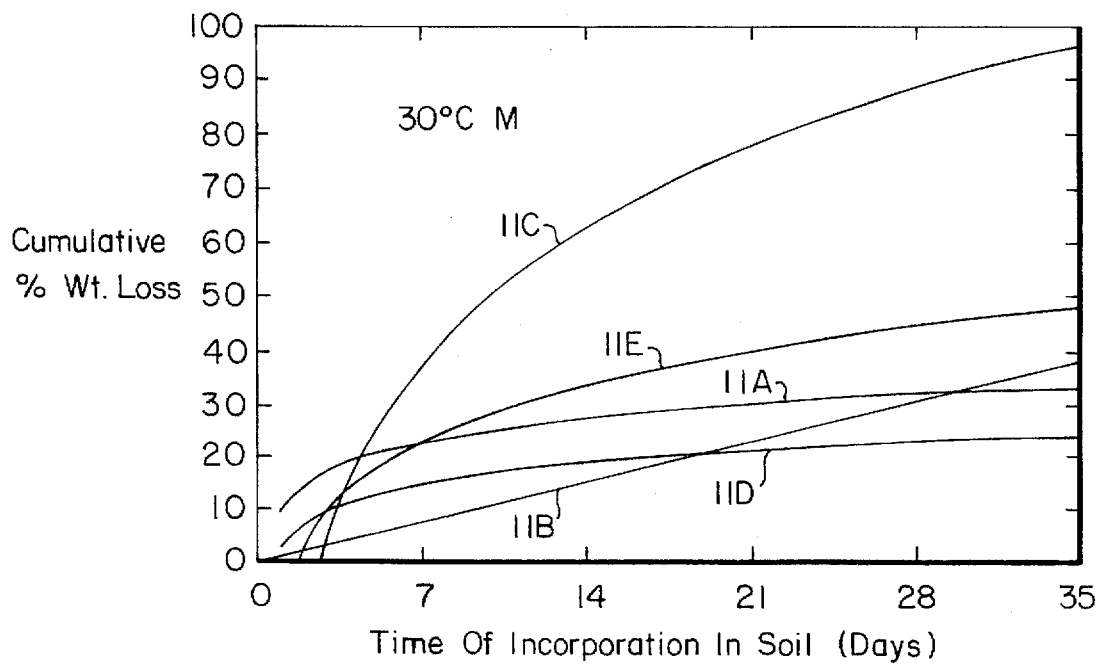
FIGS. 11 and 12 show the effect of the incorporation of fillers on the degradation rate of the biodegradable matrix.

FIG. 11 shows the effect of the addition of a variety of fillers on the degradation rate and total weight loss of a matrix, other factors being constant.

Figure 12:
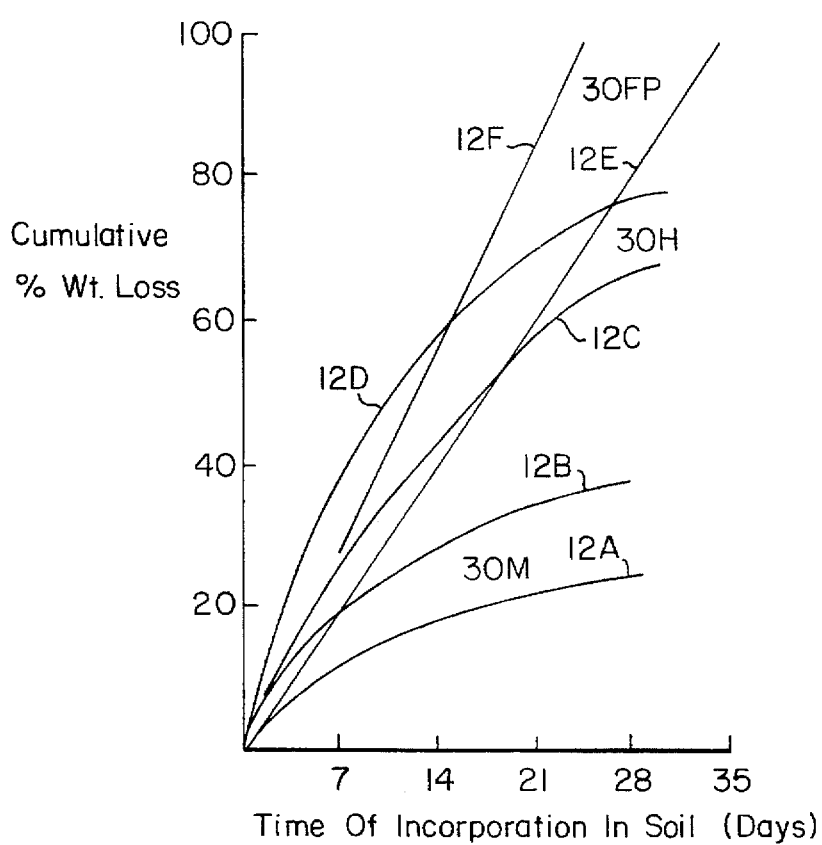

The rate of degradation and total weight loss of the matrices of FIG. 11 as a function of soil moisture is illustrated in the family of curves of FIG. 12 wherein, a) the region between lines 12A and 12B represents the degradation rates and total weight losses of the matrices of FIG. 11, but excluding the formulation 11C. comprising 10% $(NH_4)_2SO_4$, under medium (M) soil moisture conditions at a soil temperature of 30° C.;

b) the region between lines 12C and 12D represents the degradation rates and total weight losses of the matrices of FIG. 11 under high (H) soil moisture conditions at a soil temperature of 30° C.; and c) the region between lines 12E and 12F represents the degradation rates and total weight losses of the matrices of FIG. 11 under flood plot (FP) conditions at a soil temperature of 30° C.

From the Figures it is evident that with the exception of the formulation comprising 10% $(NH_4)_2SO_4$, both the amount and rate of degradation and total weight loss observed for each formulation were substantially the same, regardless of the level of soil moisture present. However, the weight loss exhibited by the formulation comprising $(NH_4)_2SO_4$ suggests that degradation was not just a result of dissolution of this water soluble filler.

Figure 13:
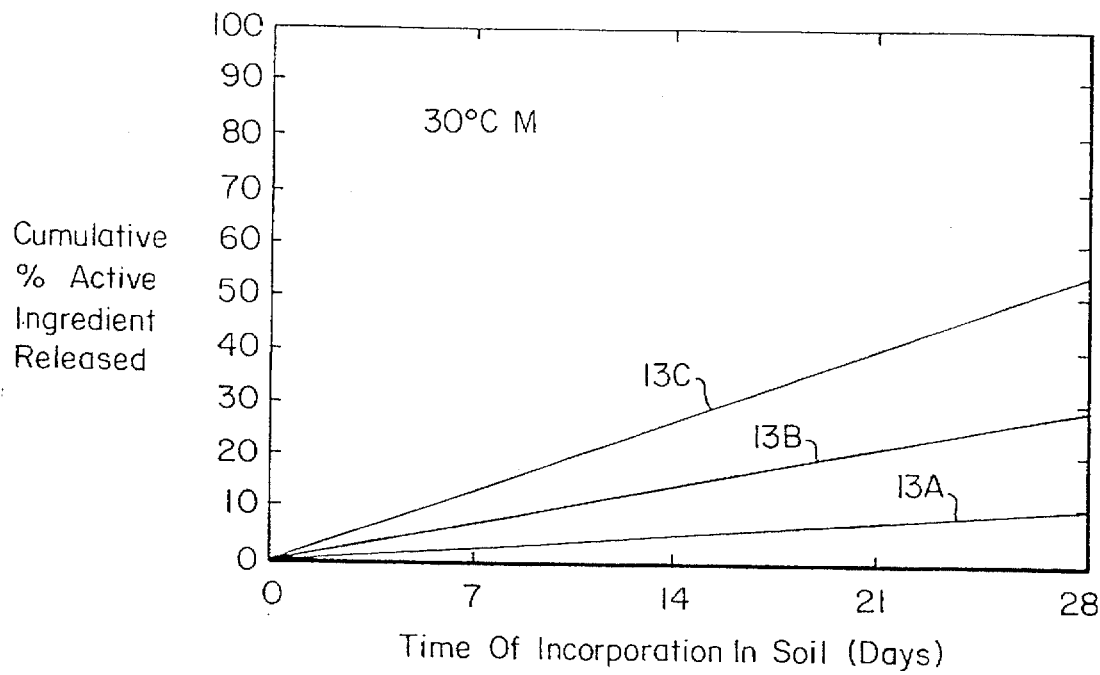
FIG. 13 shows the variation in the release rate of the active agent that may be obtained by the selection of either carbosulfan, chlorpyrifos or phorate.

The nature of the active agent will affect its rate of release. This is because different active agents will release at different rates under the same conditions, depending upon their water solubility, partition coefficients, cohesive energy densities, molecular size and other physical and chemical properties. FIG. 13 shows the variation in release rates obtained where three different active agents were compared.

Figure 14:
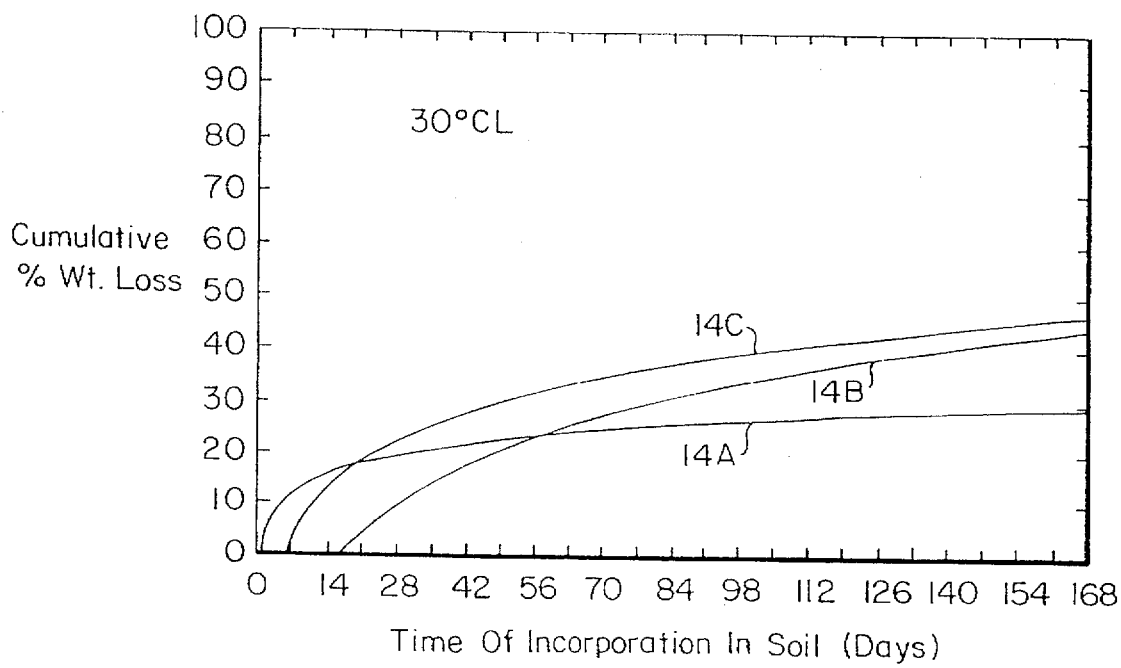
FIG. 14 shows the effect of the introduction of an active agent on the degradation rate of the biodegradable matrix.
Figure 15:
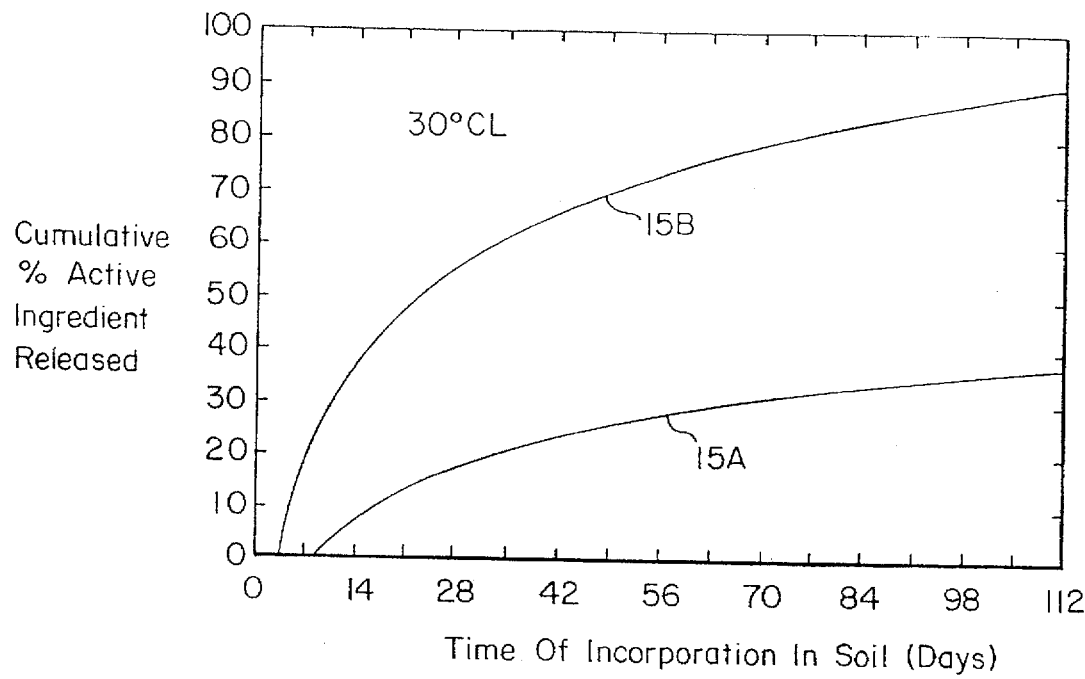
FIG. 15 shows the release rate of the active agent from those matrices from FIG. 14 including an active agent.

FIGS. 14 and 15 show that the release rate of any active agent is substantially independent of the biodegradation rate of the matrix. FIG. 14 shows the cumulative % weight loss of three matrices whereas FIG. 15 shows the cumulative % weight loss of the respective active agents from the corresponding matrices shown in FIG. 14 under the same conditions.

Figure 16:
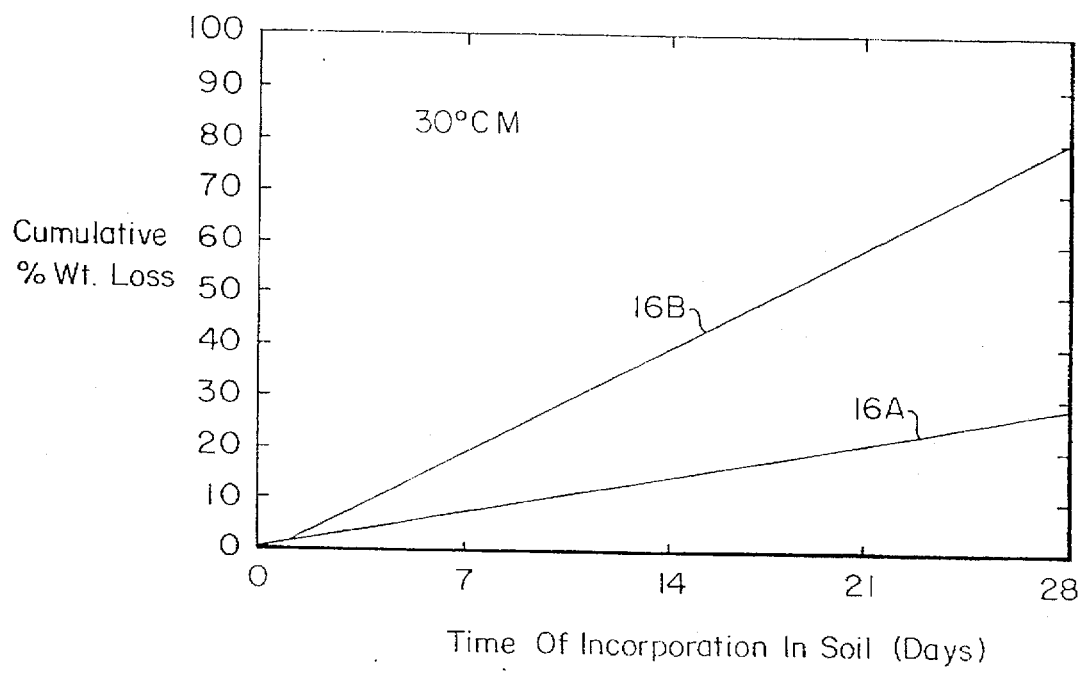
FIG. 16 shows the effect of the addition of 9% filler [$(NH_4)_2SO_4$] on the release rate of the active agent.

In any event, the release rate of a given active agent may be varied by the selection of different amounts of the agent or the inclusion in the formulation of release rate modifiers such as fillers, synthetic polymers and the like. FIG. 16 illustrates a modification to the release rate that may be achieved by comparing the total % weight loss of an active agent from a matrix comprising about 9% w/w ammonium sulphate (16B) with the total % weight loss of the same active agent from a similar matrix (16A). That graph clearly shows that incorporation of $(NH_4)_2SO_4$ in the formulation increased the release rate of the active agent over the specified time period.

In summary, by selecting the appropriate starting materials and processing conditions, the release rates and degradation rates of the matrices according to the invention can be tailored for use in a range of environments so as to exhibit desired release rates and degradation rates.

The amylaceous material or derivatives thereof used in this invention do not undergo destructurization during the manufacture of the biodegradable matrix shapes in which they are incorporated.

This is illustrated in the following experiments.

Experiment 1

Two formulations of the soil insecticide, chlorpyrifos were chosen for this evaluation. The formulation used is given in Table 2.

TABLE 2

| | | Formulation details | | | | | |
|---|---|---|---|---|---|---|---|
| | | | | Composition | | | |
| Formul. No. | Batch No. | Starch A948 | G 50 | Glycerol | Water | Attapulgite | Corvic 6733 | Chlorpyrifos |
| G01S05 | 014241 | 63.9 | — | 4.0 | 17.3 | 4.5 | — | 10.3 |
| G01S09 | 024243 | — | 60.2 | 4.0 | 16.0 | 4.5 | 5.0 | 10.3 |

Starch A948 is sourced from Starch Australasia Ltd as a octenyl succinated high amylose maize starch, with minimum 80% amylose and succinyl value 2–3.

Starch Gelose 50 (G 50) is sourced from Starch Australasia Ltd as an unmodified high amylose, with Min. 50% w/w amylose.

Corvic 6733 is sourced from ICI Australia Operations Pty Ltd, as a medium molecular weight grade polyvinyl chloride, with ISO 'K' Value 67, Average apparent density 530 g/liter, and Total volatile matter less than 0.25% (Weight reduction, 1 hr/135° C.).

Attapulgite is sourced from Mallina Holdings Ltd, as a Attapulgite grade 080 F, with 85–90 % w/w passing 160 micron, mean particle size 35 micron.

Glycerol is commercial grade glycerol available from a number of sources.

Chlorpyrifos Technical is Dursban FM technical (96% minimum) supplied by Dow Elenco.

The formulations differ with the incorporation of minor component of a synthetic polymer (polyvinyl chloride in this case) in one formulation and the use of chemically modified and unmodified starches. The residual moisture levels in the starches used in these formulations has been measured as follows.

| | |
|---|---|
| A948 | 12.0% w/w water |
| G 50 | 12.5% w/w water |

This will give the following moisture levels in the raw material blend feed to the extruder:

| | |
|---|---|
| Formulation G01S05 | 29.3% w/w water |
| Formulation G01S09 | 28.5% w/w water |

Process description

All the materials (including liquids) used in the formulation were blended for 10 minutes at ambient temperature in a high speed Prodex blender to form a free flowing homogeneous powdered mixture.

The blend was then fed to a Betol BTS 40L twin screw co-rotating intermeshing extruder having six barrel segments, each with separate electric heater and cooling supply. A die with 2 mm diameter die holes containing bend electric heater. The extruder screws were of constant root diameter width a length diameter ratio of 25:1. Both formulations were cooled in air to form strands and pelletized in a rotary pelletiser (Cumberland manufacture) form the desired sized pellets, in a continuous process.

Extrusion conditions

Both formulations were extruded at the same extrusion conditions. The screw speed was 160 RPM, feed rate 15 kg/hr, extrusion temperatures 75°–90° C, extruder motor load 7–12 AMPS, and extrusion pressure of 600–850 psi. Detailed extrusion conditions are given in Table 3.

TABLE 3

Extrusion conditions

| Extrusion Parameters | | Formulation G01S05 | Formulation G01S09 |
| --- | --- | --- | --- |
| Extruder | Zone 1 | 75/75 | 75/76 |
| | Zone 2 | 77/78 | 77/79 |
| Barrel Zones | Zone 3 | 80/80 | 80/81 |
| Temperatures | Zone 4 | 83/83 | 83/84 |
| Set/Actual [°C.] | Zone 5 | 86/87 | 86/87 |
| | Zone 6 | 90/91 | 90/91 |
| Die Temperature Set/Actual [°C.] | | 90/90 | 90/91 |
| Extruder | Zone 4 | 0 | 0 |
| Vacuum [−KPa] | Zone 5 | 0 | 0 |
| | Pressure [psi] | 770 | 820 |
| | Speed [RPM] | 160 | 160 |
| | Load [AMPS] | 7 | 12 |
| Palletizer | Puller | 155 | 155 |
| | Cutter | 007 | 007 |
| Pellet size [L × D] | | 2.0 × 1.8 | 2.0 × 1.8 |
| Feed Rate [kg/hr] | | 15 | 15 |

Release Rate & Degradation testing and Effect of Formulation

The release rate and degradation test were conducted in controlled environment at temperatures 15° C. and 30° C. and 3 separate watering regimes to obtain low, medium and high moisture according to the following technique.

A Technique for Characterising Soil-Applied Controlled Release Pesticide, Biodegradable Formulations

INTRODUCTION

This method is suitable for testing release of active ingredient and degradation (weight loss) controlled release (CR) formulations where there exists a possibility of change of weight during the trial caused by the following factors:

degradation of matrix leaching soluble filler from matrix absorption of water soil on the surface of recovered granules, and leaching of plasticiser from the matrix Formulations where results could be influenced by any of the above factors should be tested according to this method.

GENERAL DESCRIPTION OF OPERATION

The release rate test station consists of two temperature controlled environments (30° C., 15° C.) vans. Each temperature controlled van is divided into 3 separate watering regimes:—Low (temperate), Medium (subtropical) and High (tropical).

The low watering zone in both temperature environment assimilates 128 mm rainfall per annum and is operated such that moisture content of soil is varied from 47% above the field capacity to the wilting point of the soil.

The medium watering zone delivers the equivalent of 510 mm in the 30° C. environment and 255 mm in the 15° C. environment per annum and operates such that moisture content of the soiled is varied from 67% above the field capacity to 59% below field capacity.

The high watering zone delivers the equivalent of 510 mm in the 30° C. environment and 255 mm in the 15° C. environment per annum and operates such that moisture content of the soils varied from 230% above field capacity to 117% above field capacity.

Environmental conditions are monitored daily: van humidity, soil temperature, soil moisture, van temperature, irrigation type and date.

SAMPLE PREPARATION

Sample granules need to be sieved to obtain particle size (particle size distribution) as per specifications of the product. Moisture content to be adjusted by placing samples in 30° C. van in an open container for 24 hours. Supply laboratory with samples of 0.500 g±0.010 g, three replicates to obtain day 0 active ingredient content in mgr active ingredient per sample.

SAMPLE CONTAINER PREPARATION

The K-line sample jars are given four water outlet holes by means of piercing with the modified soldering iron which is set up in a drill press unit located in the Strathpine site workshop. The temperature of the soldering iron is controlled by a potentiostat.

SAMPLE ESTABLISHMENT

1. Insert a glass-wool plug in the base of the sample container
2. Add fifth grams (50 g) of sieved soil
3. Weight 0.500 g±0.010 g of sample granules and sprinkle evenly onto the soil surface.
4. Add a further fifty grams (50 g) of sieved soil.
5. Place a glass-wool plug on top of the sample jar.

30 samples to be prepared for each regime, and placed into the relevant region in the release rate test station. Containers are labelled from one to ten from left to right and details of the formulation are tagged onto the rack. The details and position of the sample formulation is then recorded.

SAMPLE RETRIEVAL

At each time point, 3 samples (R1, R2, R3) are removed and placed separately into the air forced drying oven. The glass wool plugs need to be removed from the soil surface to allow rapid evaporation and the samples are dried for 48 hours at 30° C. The sample granules are then separated from soil by using adequate sieve and brush. (Special note: It is very important to recover whole sample, every granule).

Adjust moisture content by placing granules in 30° C. van in a open container for 24 hours, then weigh them and place into labelled sealed container for laboratory testing.

ANALYTICAL TESTING

Whole sample need to be tested according to test method No. CPSC-29 and results reported as mg of active ingredient per sample. R1 and R2 samples to be tested every time and R3 if results of R1−R2=±2 mg.

DEGRADATION TEST

Recovered weight will be compared with established weight i.e. 0.500 g±0.10 g after moisture equilibration.

TREATMENT OF RESULT

Results are calculated to show cumulative % active ingredient released, and degradation as cumulative weight loss of granules as per formulas:

$$\text{Cumulative \% A.1. released} = \frac{\text{Day } 0\,A1 - \text{Day } n\,A1}{\text{Day } 0\,A1} \times 100$$

$$\text{\% Degradation} = \frac{0.5\,g - \text{Day } n \text{ weight } g}{0.5\,g} \times 100$$

Results are represented graphically (FIGS. 17–24) to show percentage of active released or degradation as a function of time.

Release Rate and Degradation of G01S05 & G01S09

FIGS. 17–20 represent release rate and degradation rate of formulation G01S05 at temperatures 30° C. and 15° C. respectively.

Figure 17:
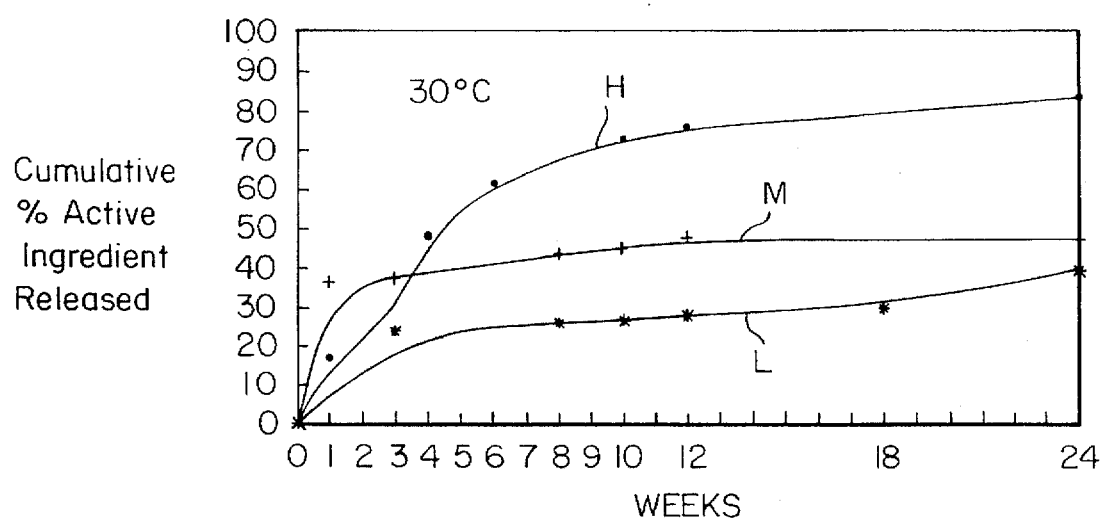
FIGS. 17 to 48 show release and degradation rates of a biodegradable matrix according to the invention.
Figure 18:
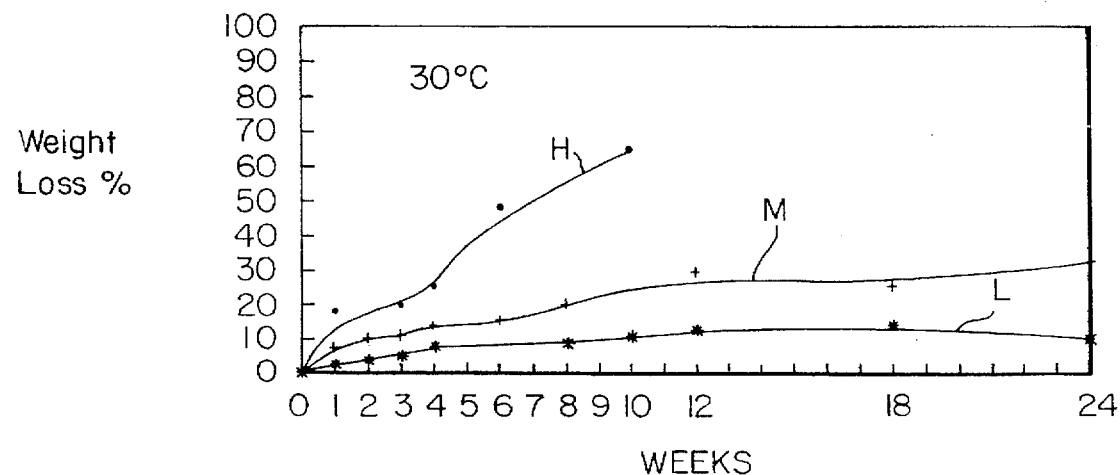

FIGS. 17 and 18 show significant influence of moisture on release rate and degradation rate at temperature 30° C.

Figure 19:
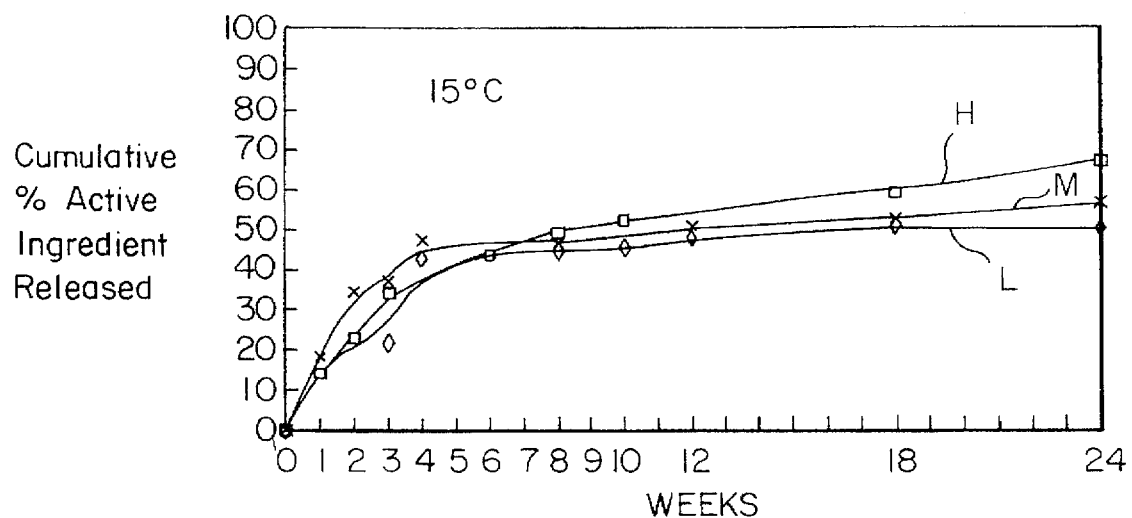
Figure 20:
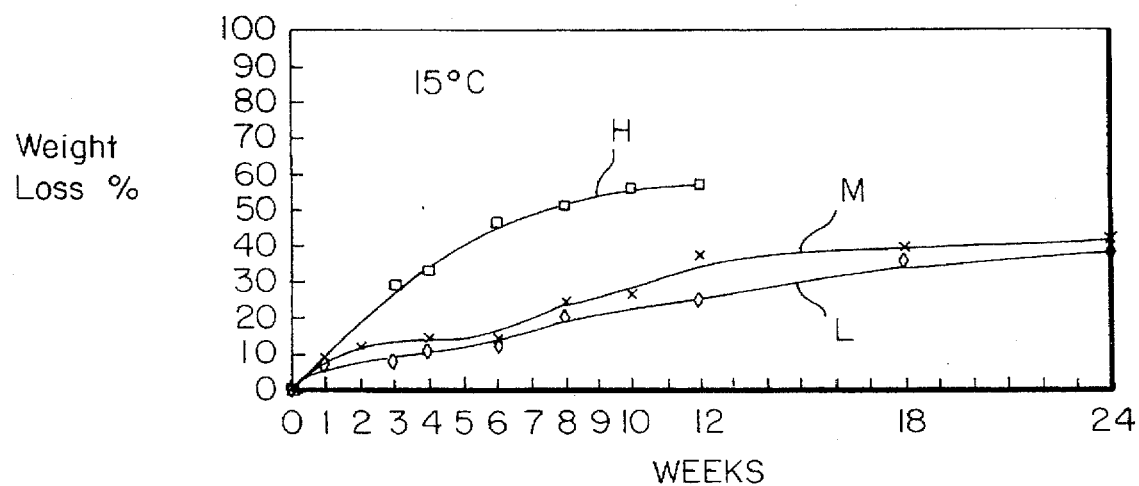
Figure 21:
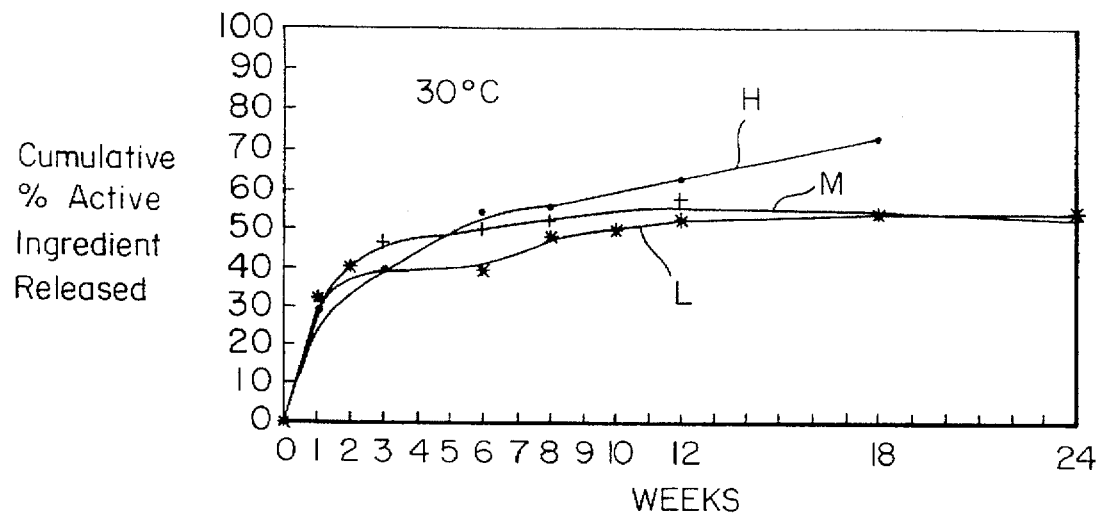

FIG. 19 shows slight influence moisture on release rate at 15° C. while degradation is much faster at high (H) moisture then at low (L) and medium (M) moisture (FIG. 20).

FIGS. 21–24 represent release rate and degradation rate of formulation G01S09 at temperatures 30° C. and 15° C. respectively.

Figure 22:
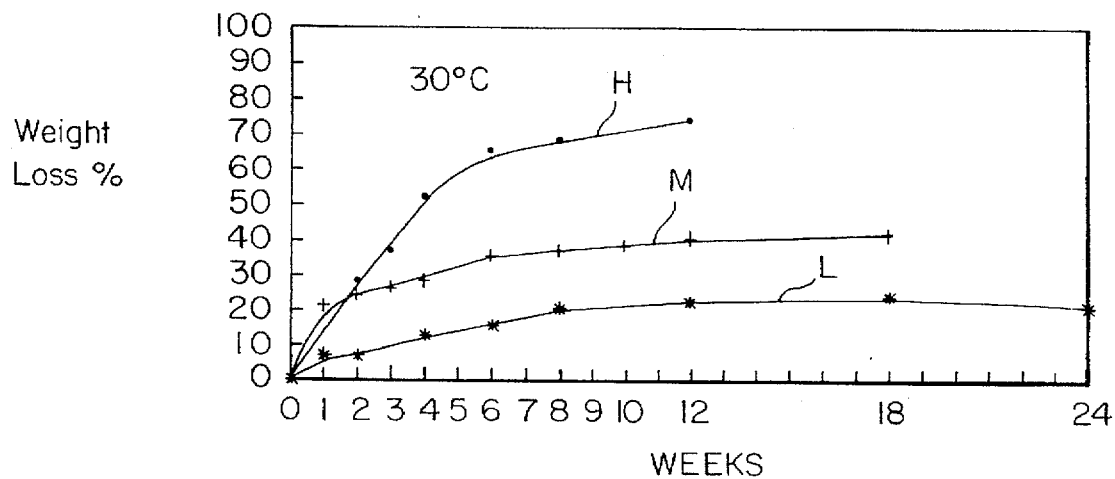
Figure 23:
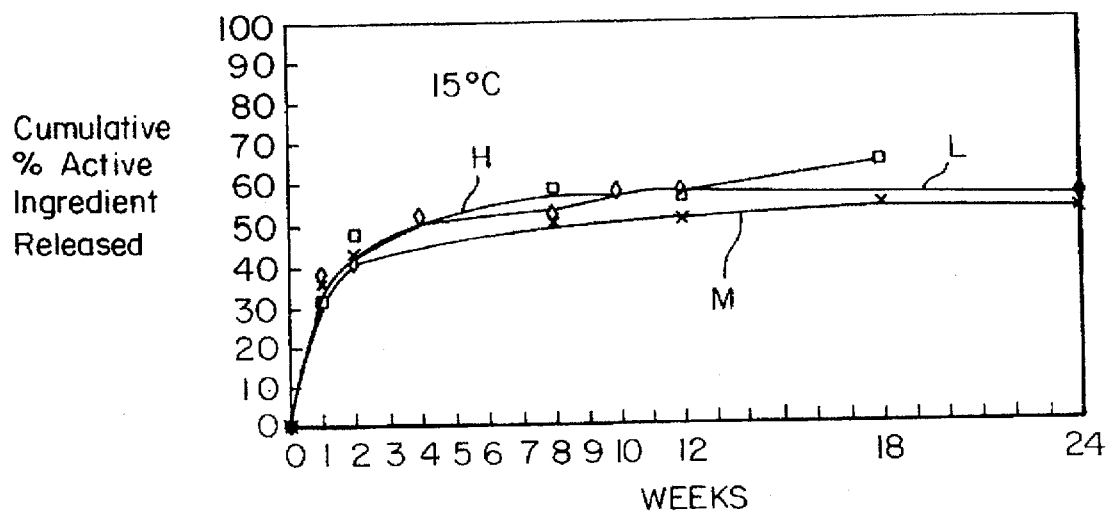
Figure 24:
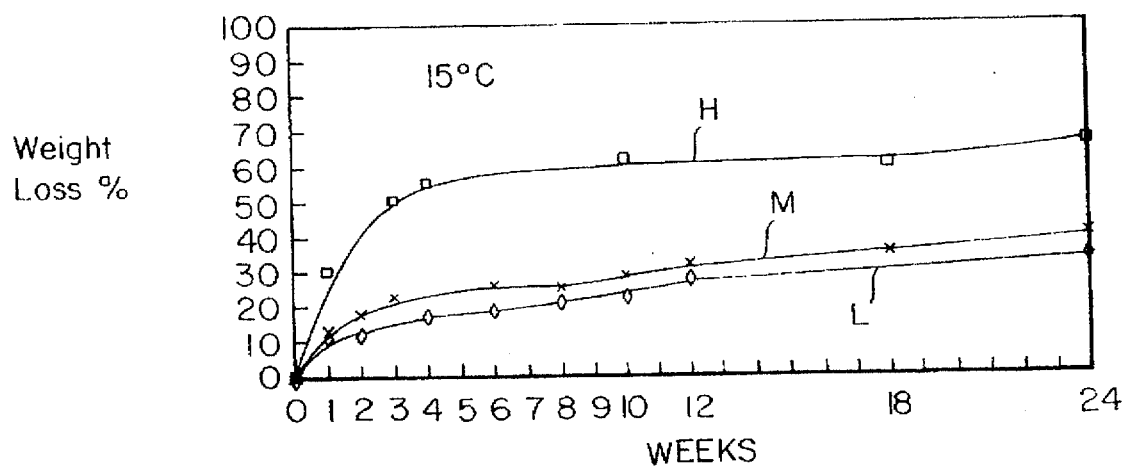
Figure 25:
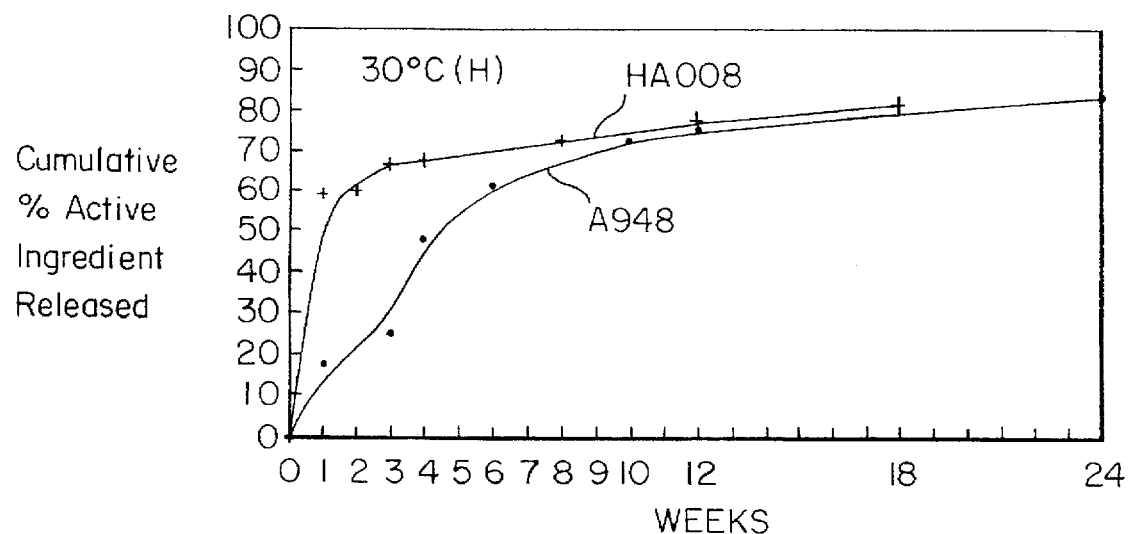
Figure 26:
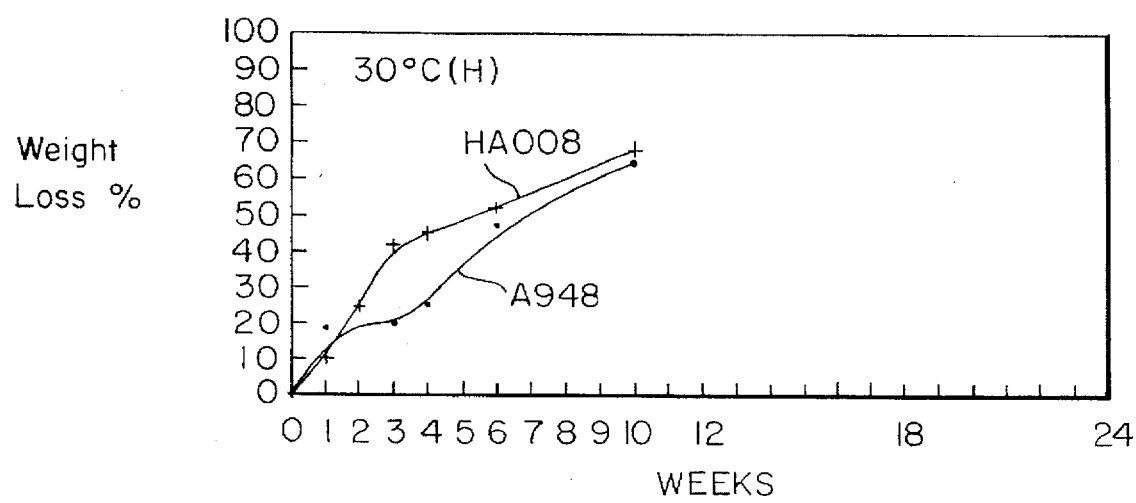
Figure 27:
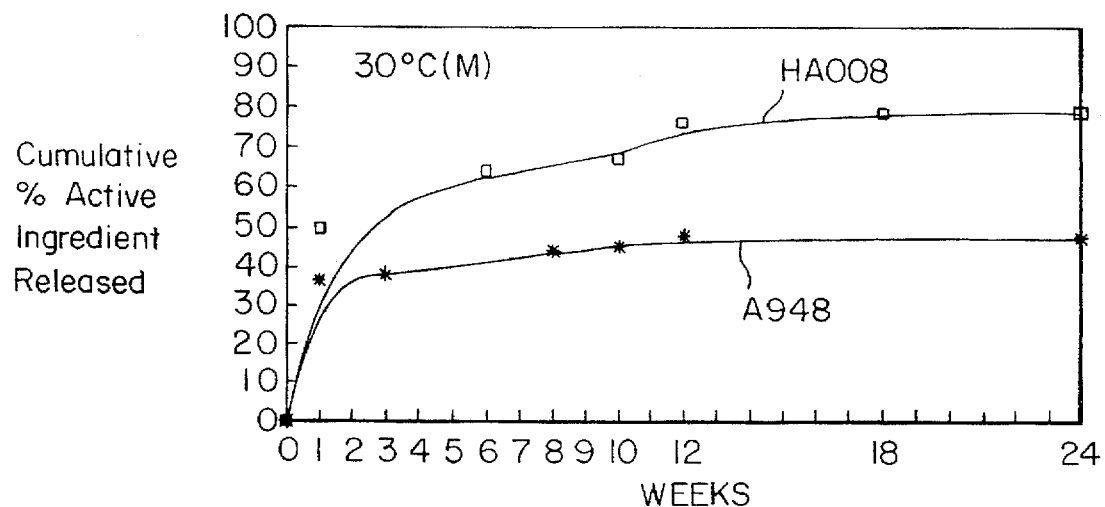
Figure 28:
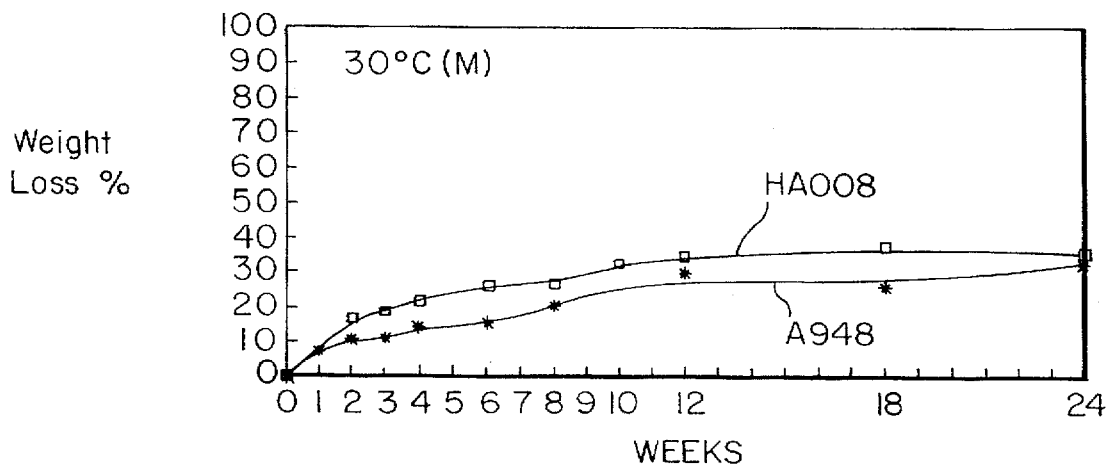
Figure 29:
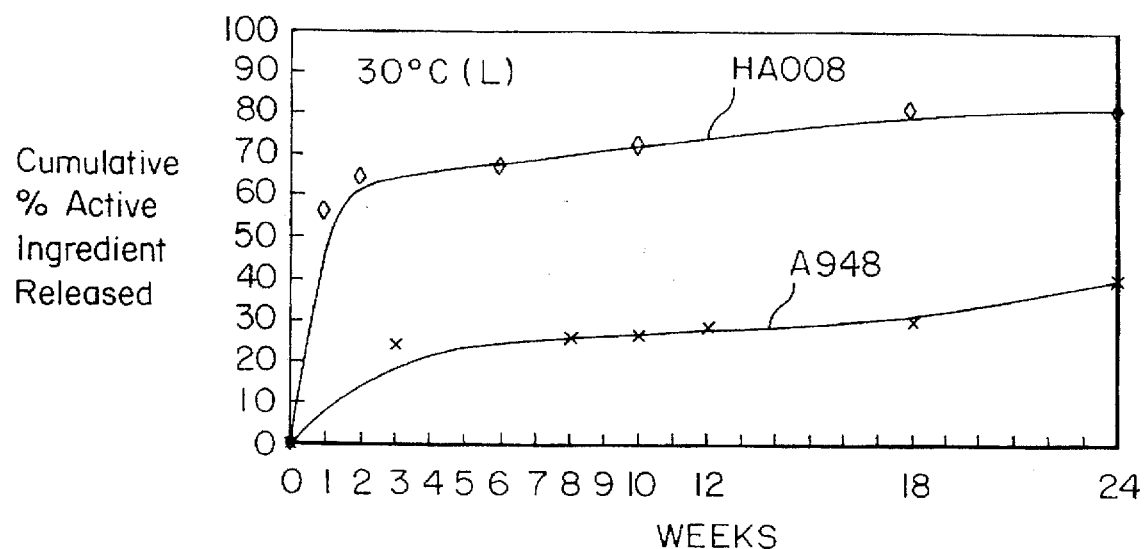
Figure 30:
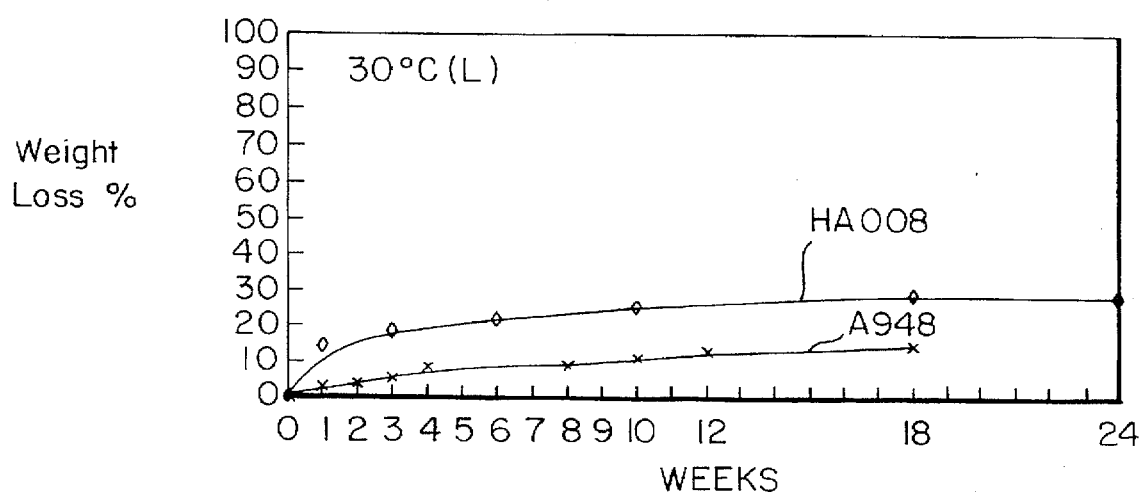
Figure 31:
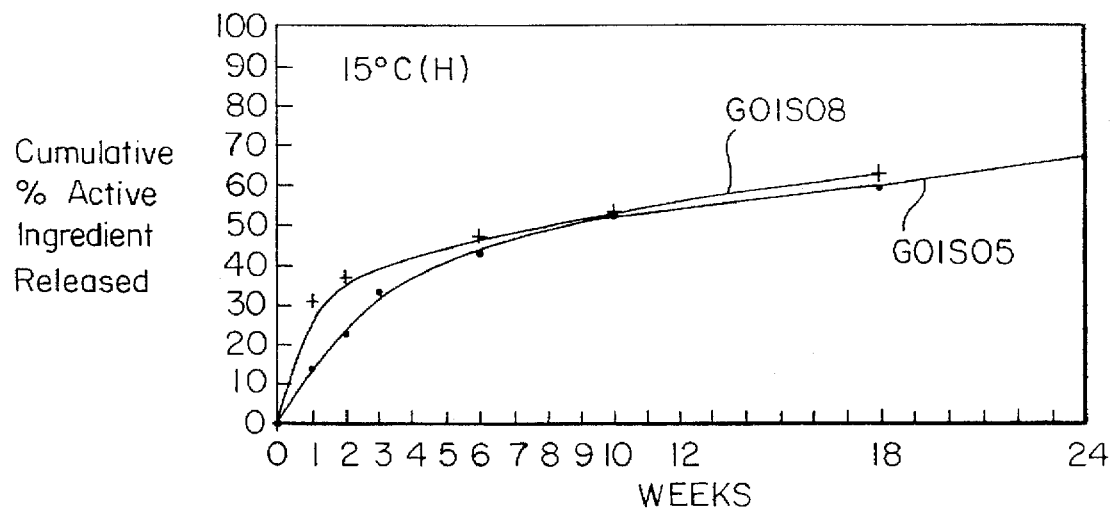
Figure 32:
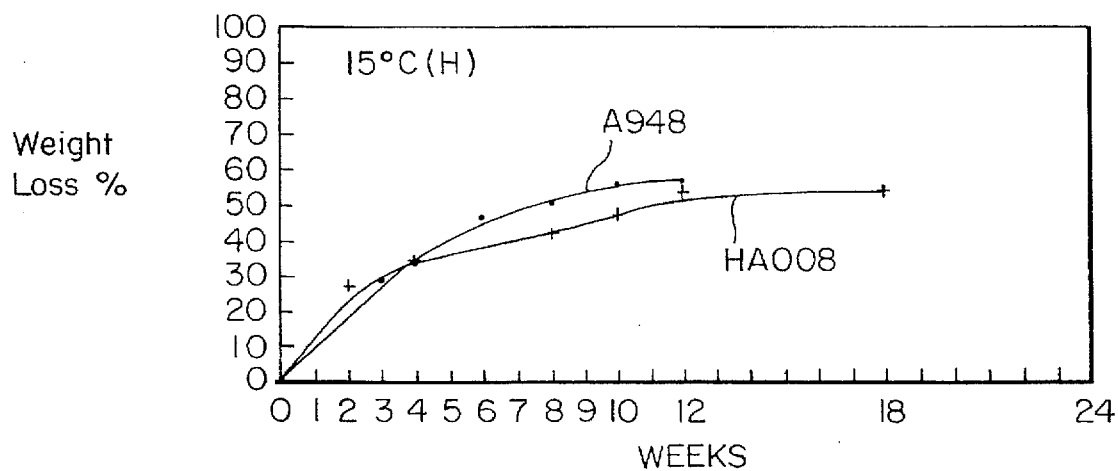
Figure 33:
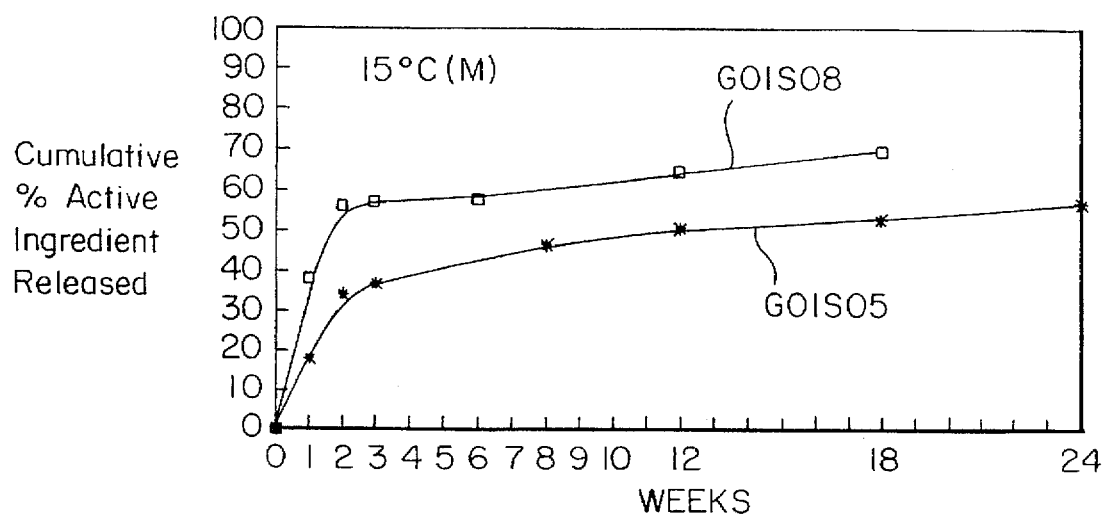
Figure 34:
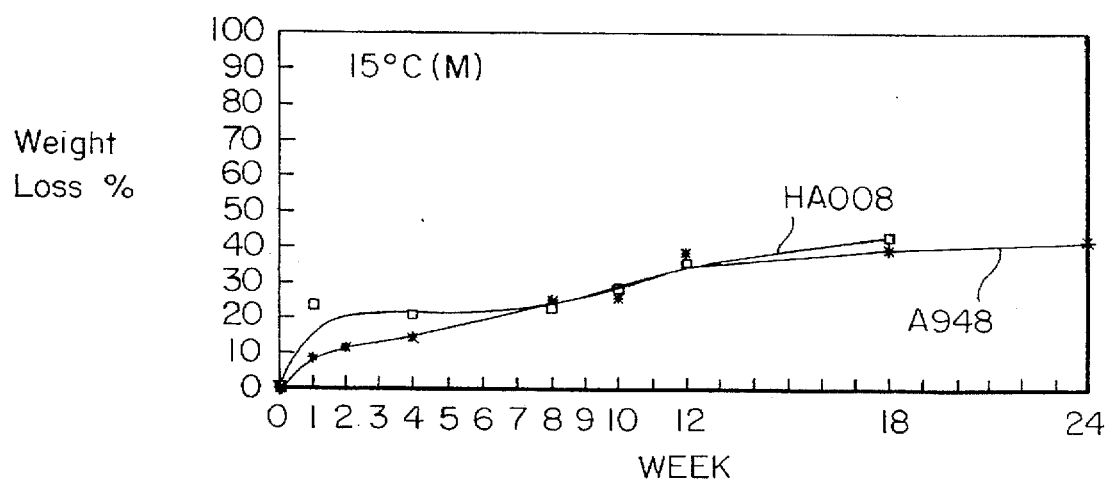
Figure 35:
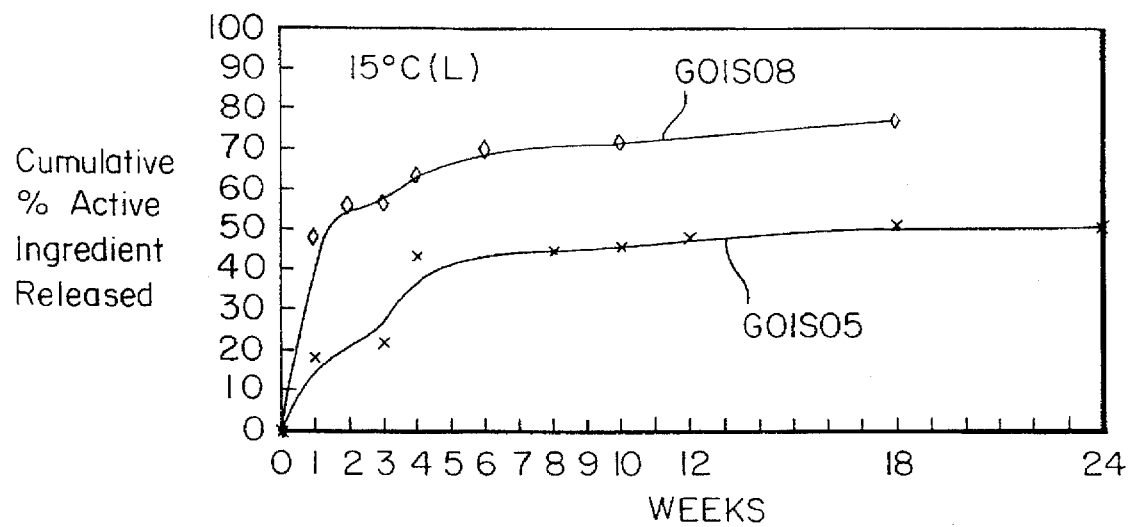
Figure 36:
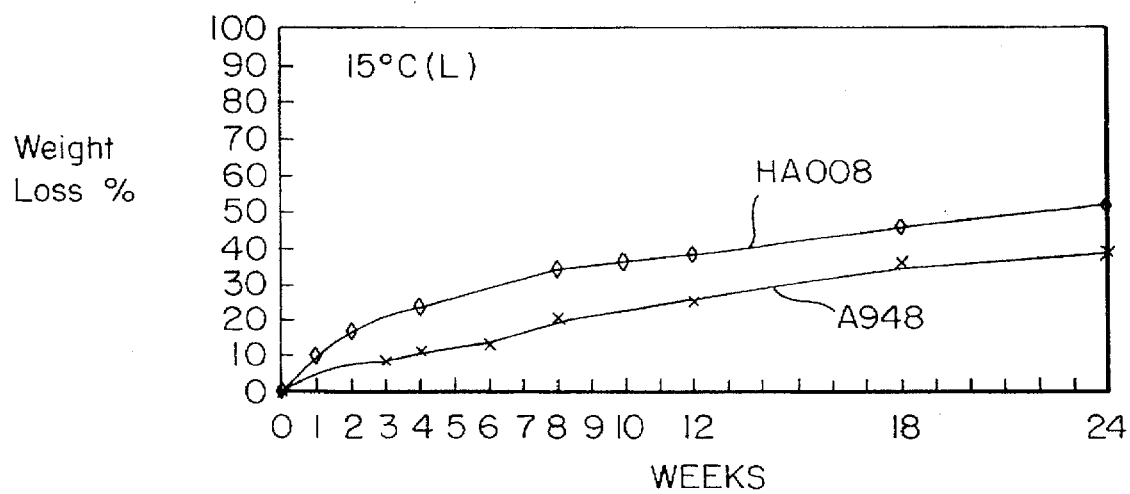
Figure 37:
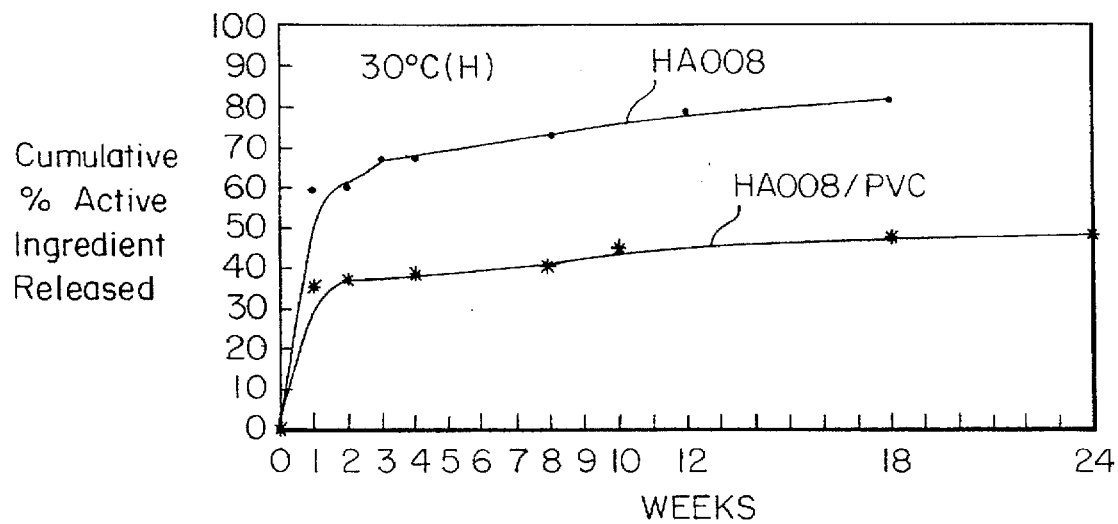
Figure 38:
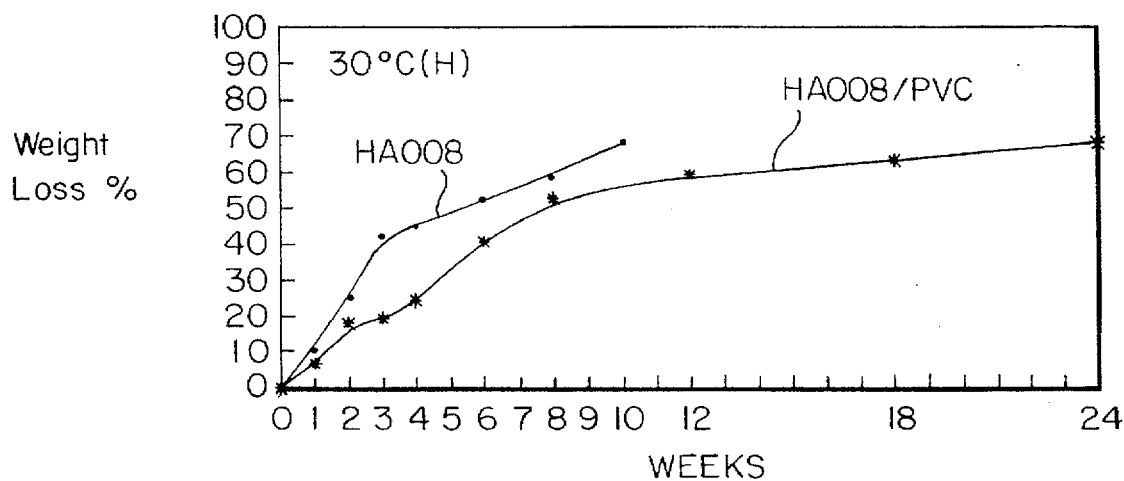
Figure 39:
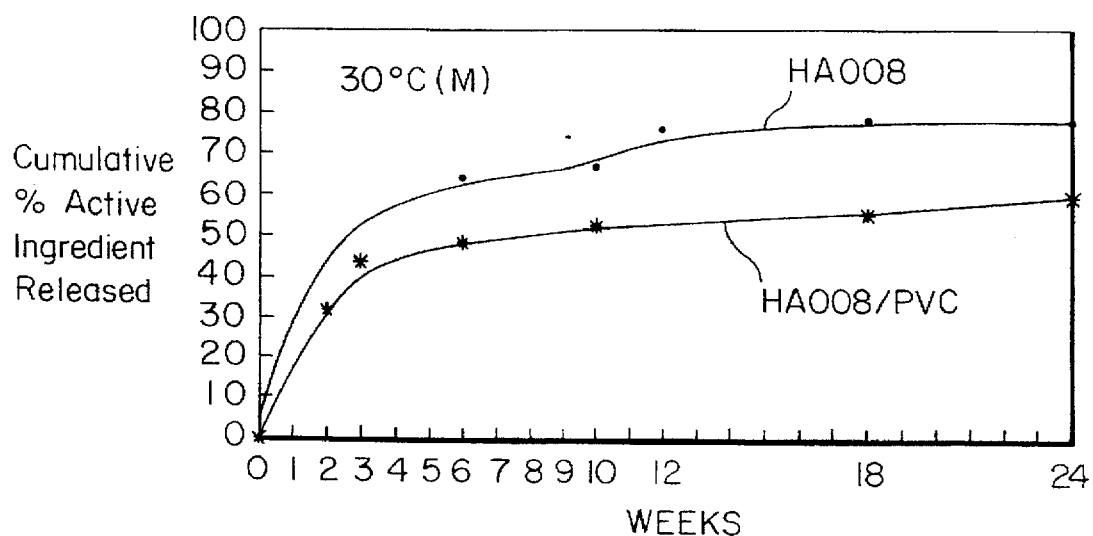
Figure 40:
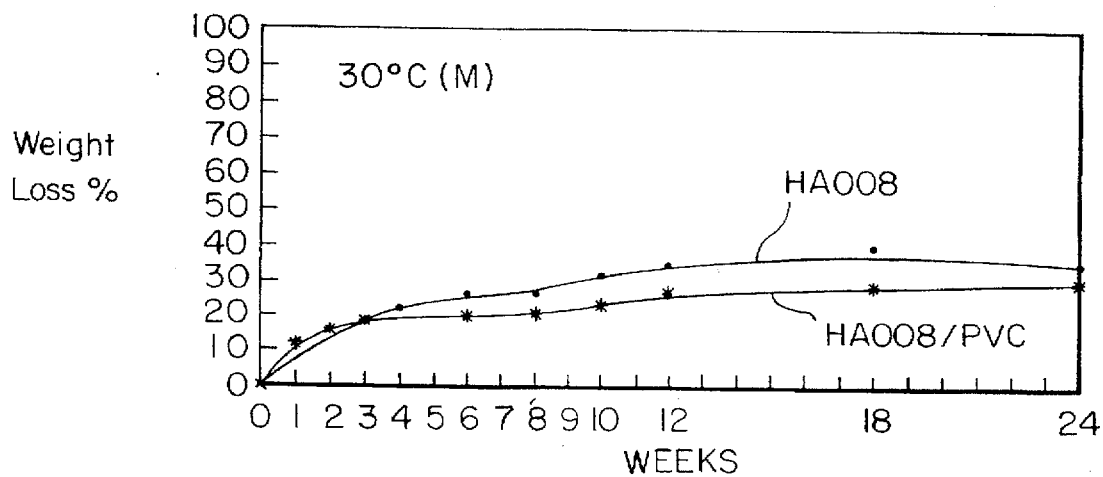
Figure 41:
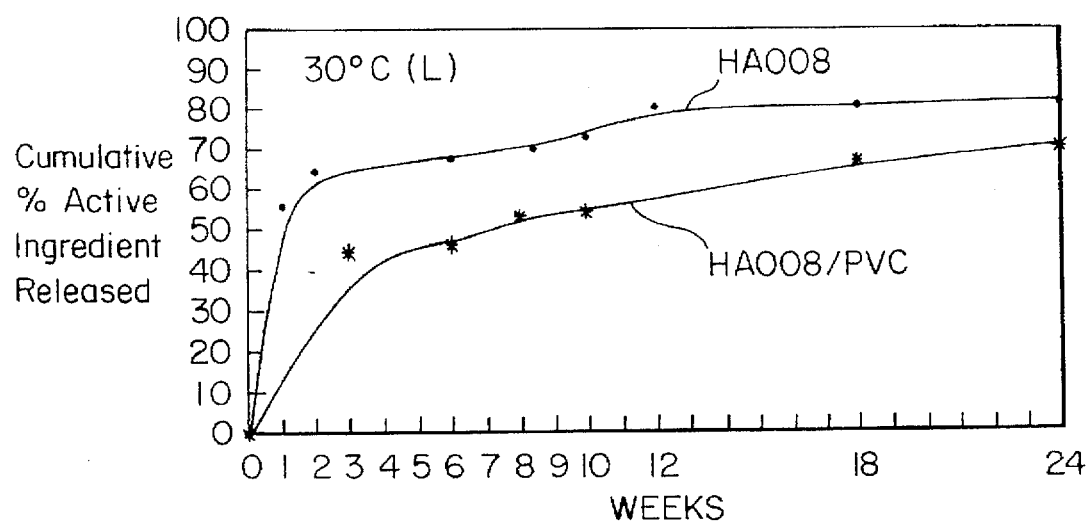
Figure 42:
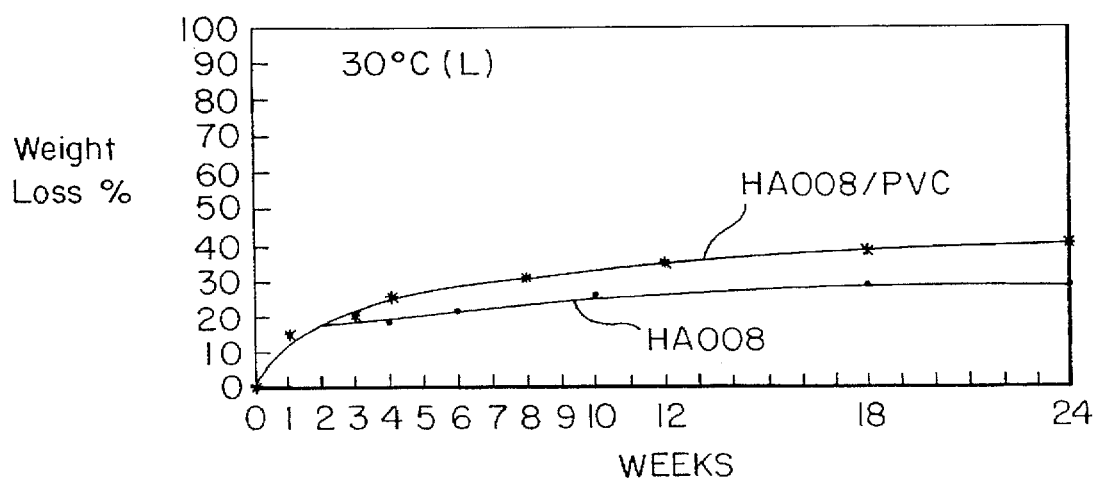
Figure 43:
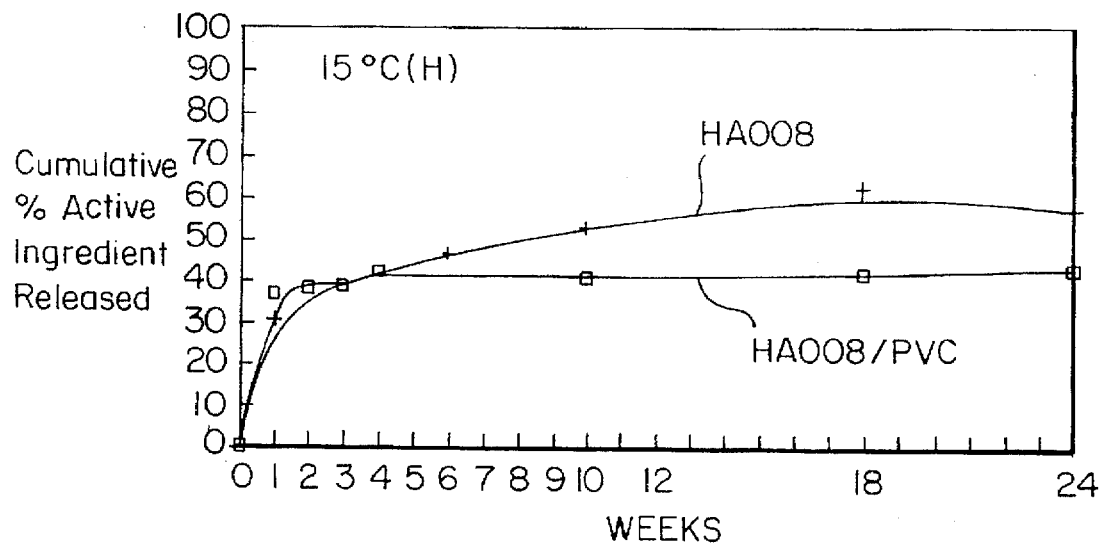
Figure 44:
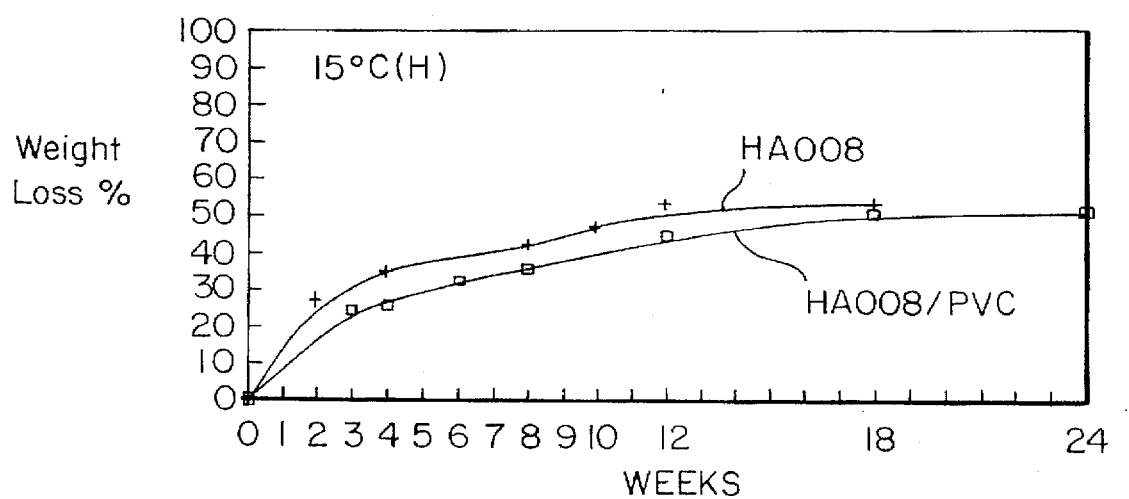
Figure 45:
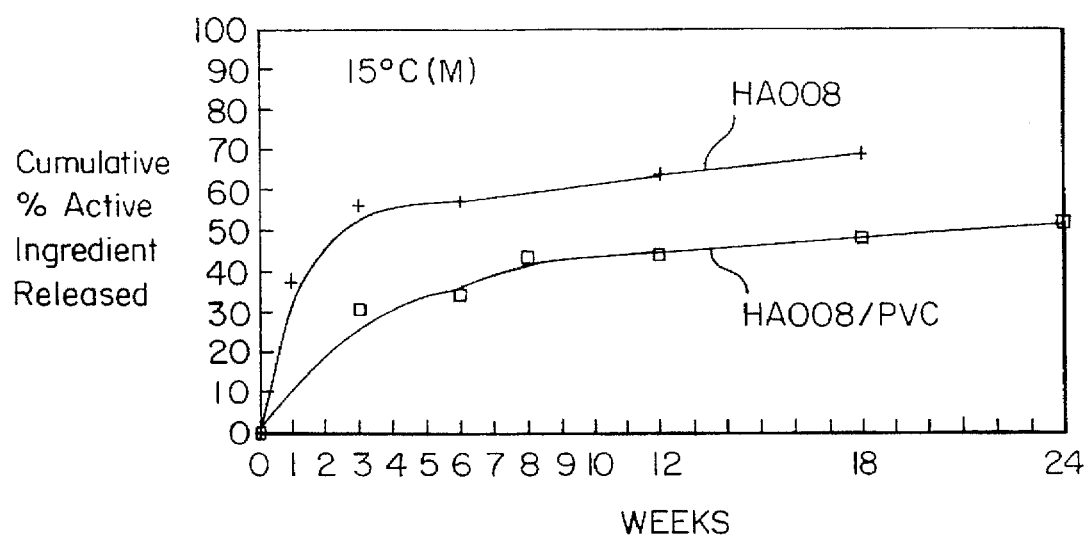
Figure 46:
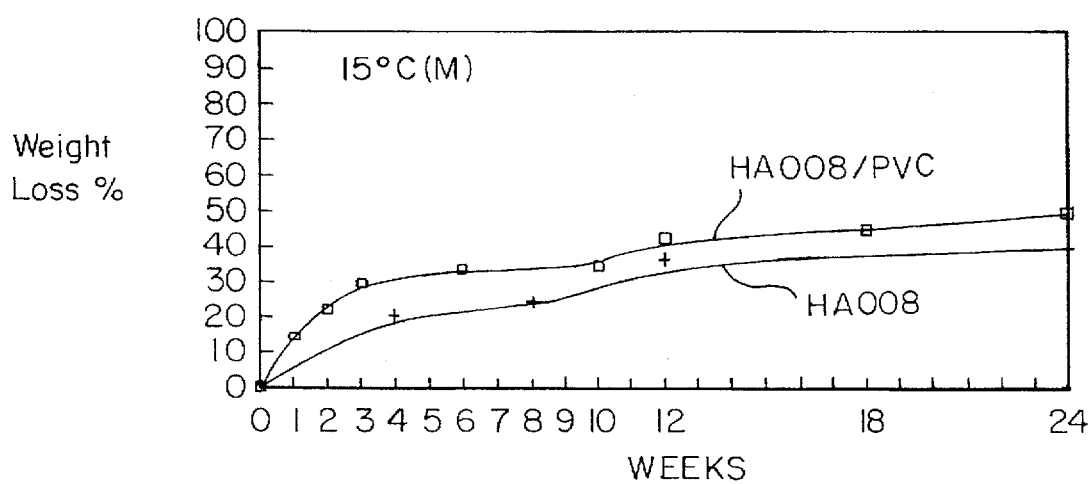
Figure 47:
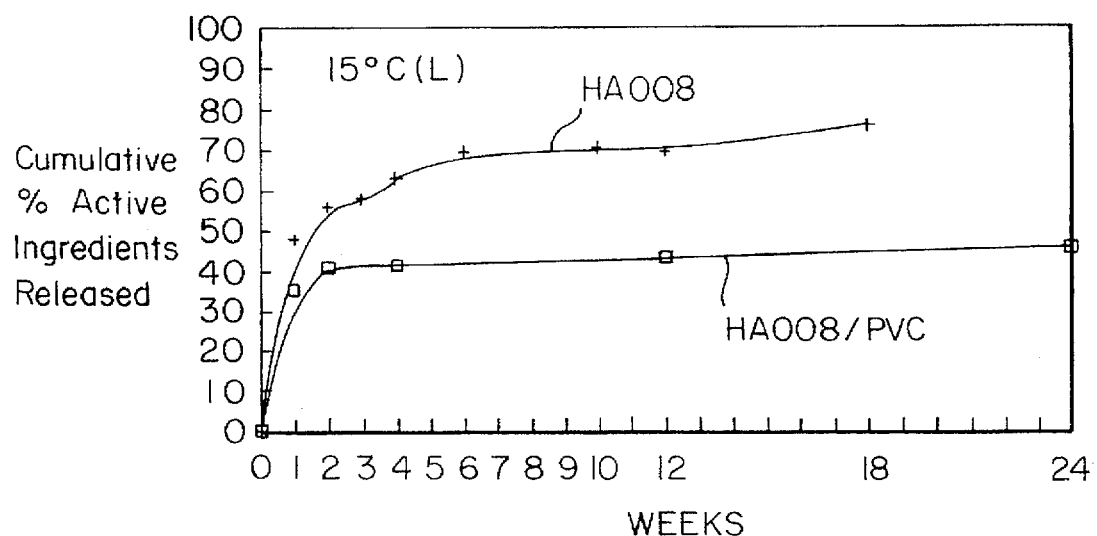
Figure 48:
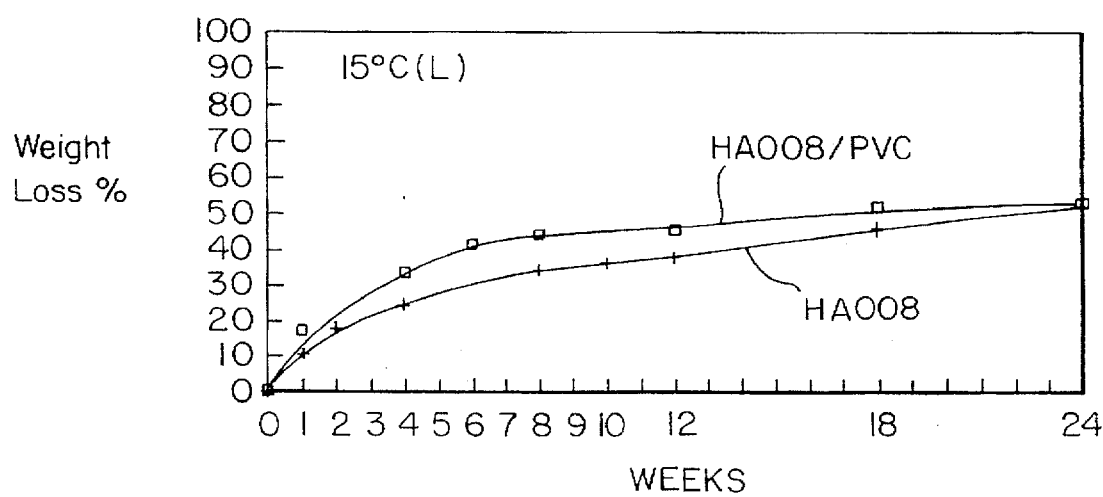
Figure 49:
FIGS. 49 to 68 are scanning electron photomicrographs of biodegradable matrices according to the present invention.
Figure 50:
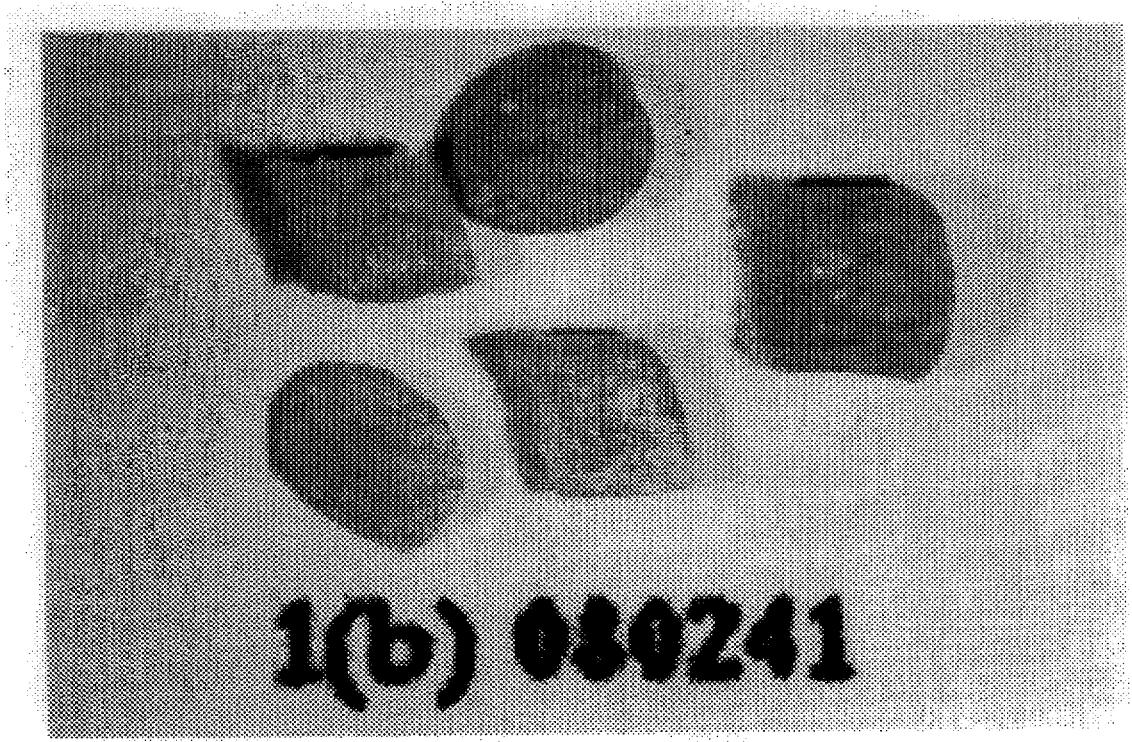
Figure 51:
Figure 52:
Figure 53:
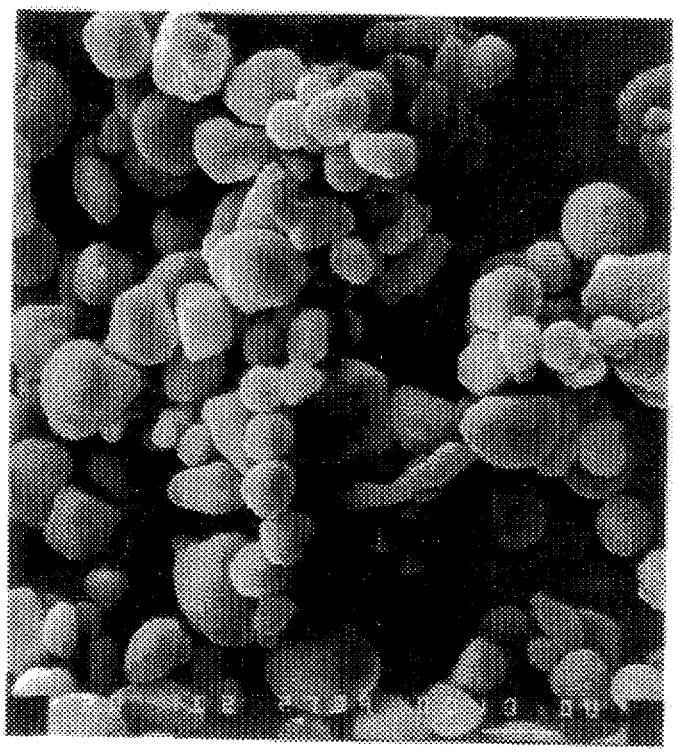
Figure 54:
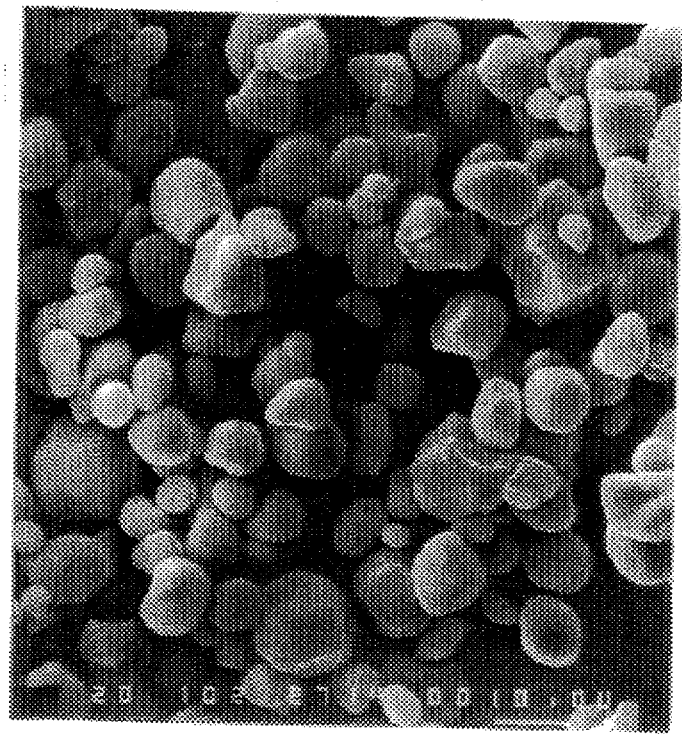
Figure 55:
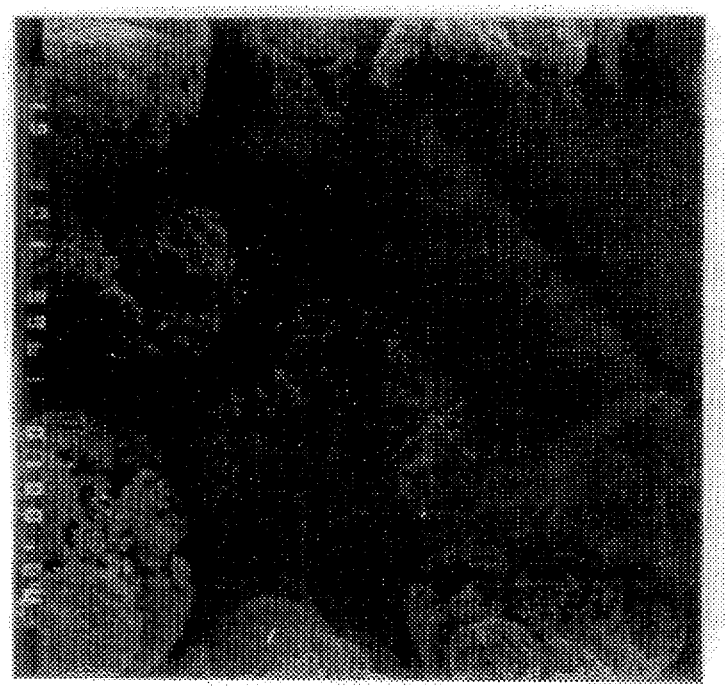
Figure 56:
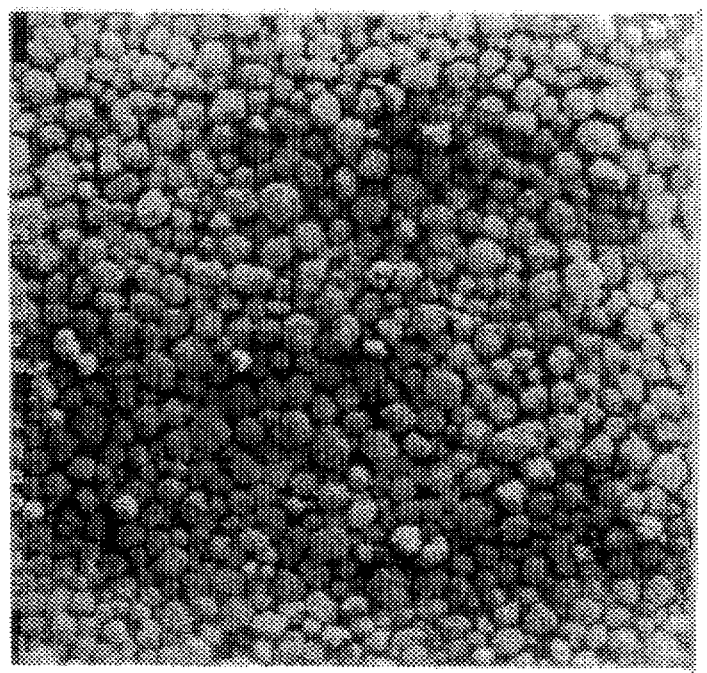
Figure 57:
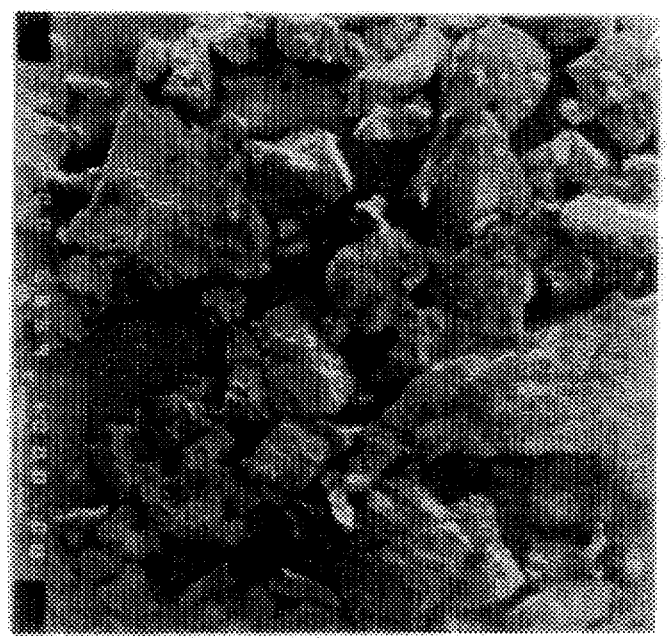
Figure 58:
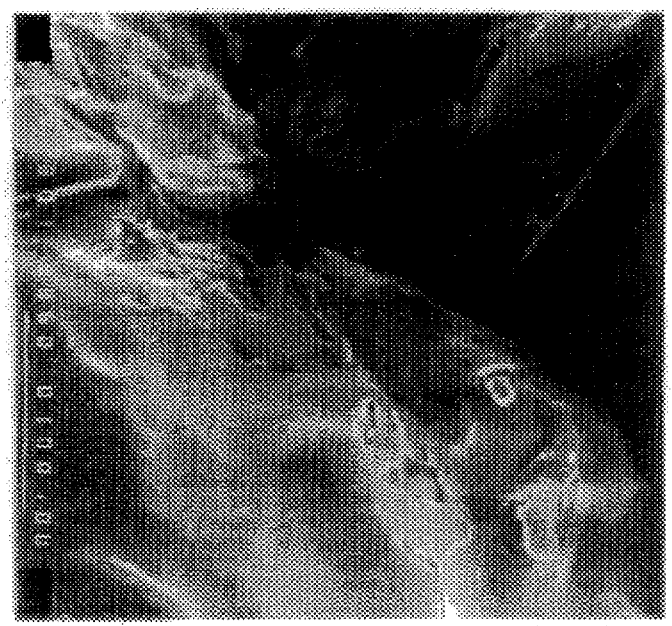
Figure 59:
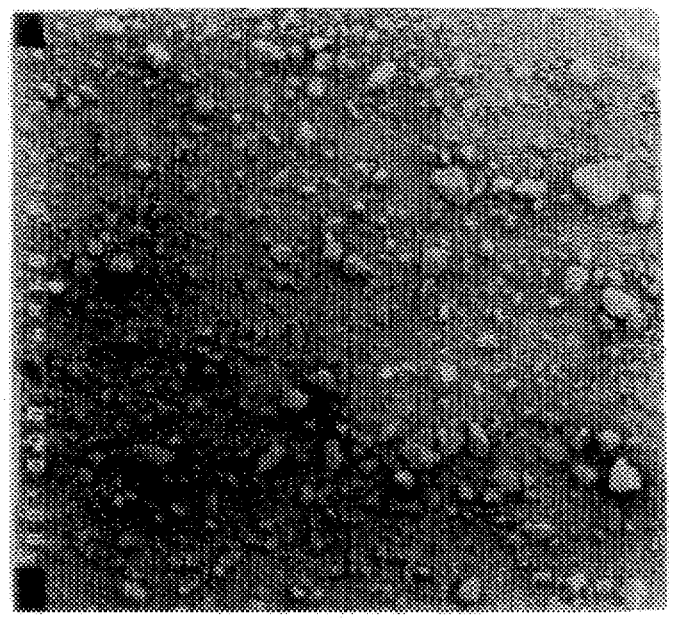
Figure 60:
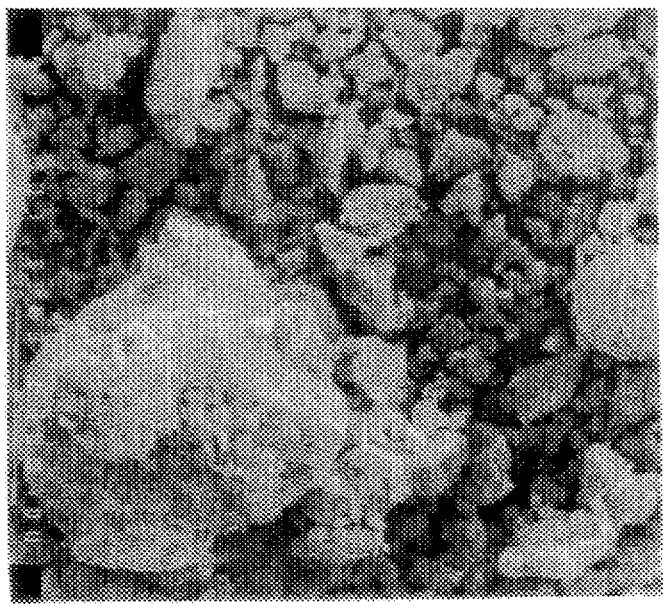
Figure 61:
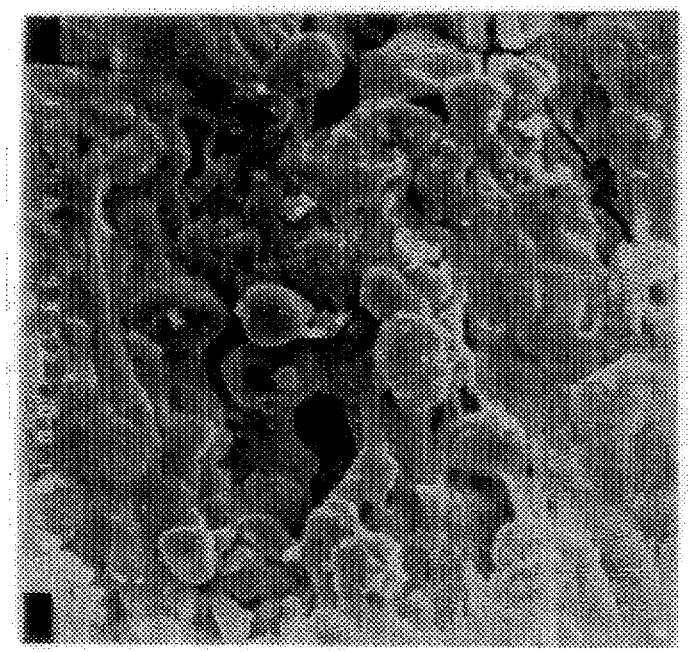
Figure 62:
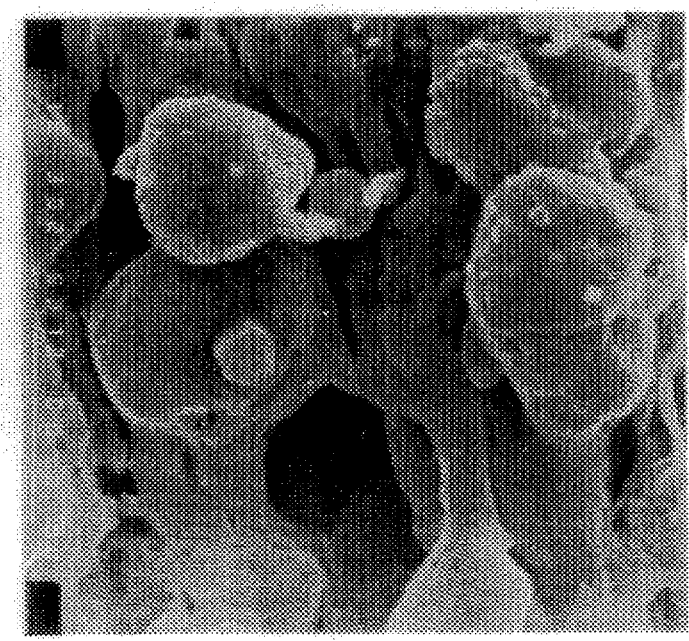
Figure 63:
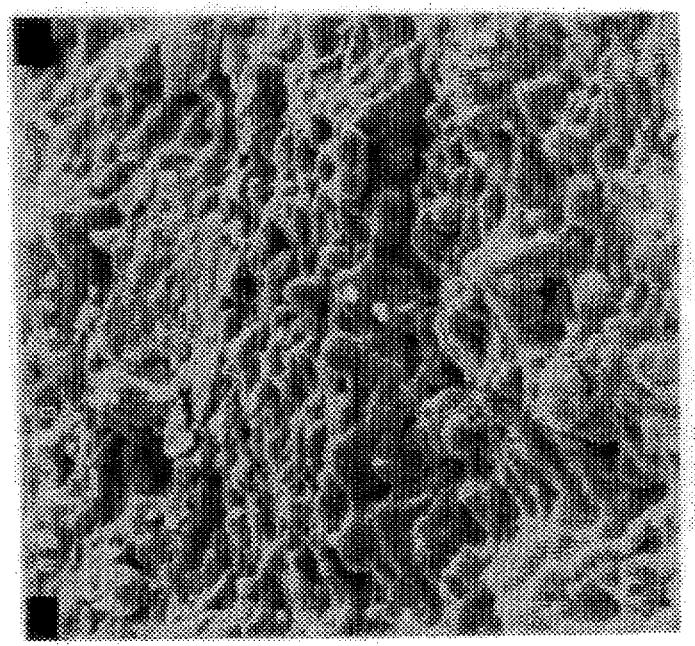
Figure 64:
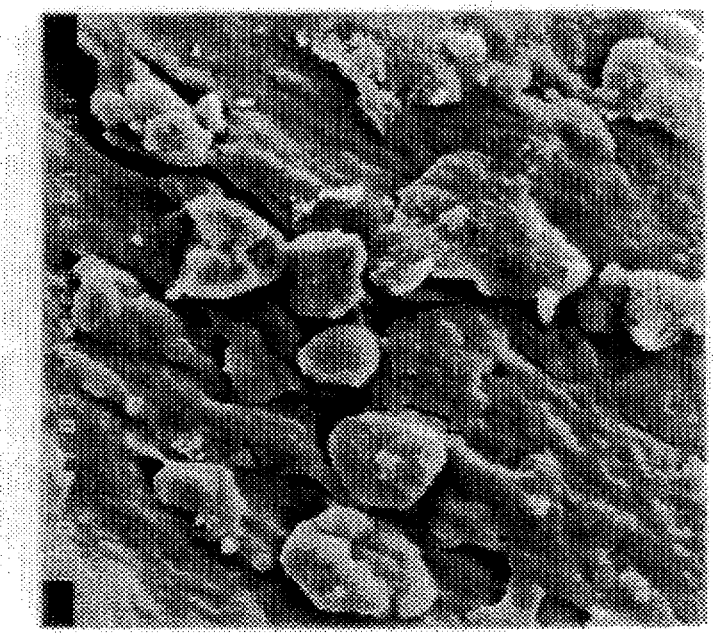
Figure 65:
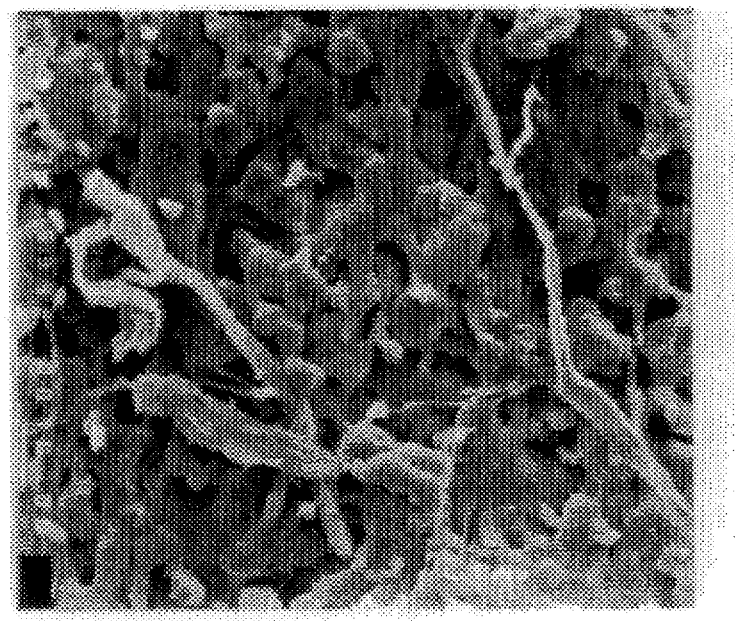
Figure 66:
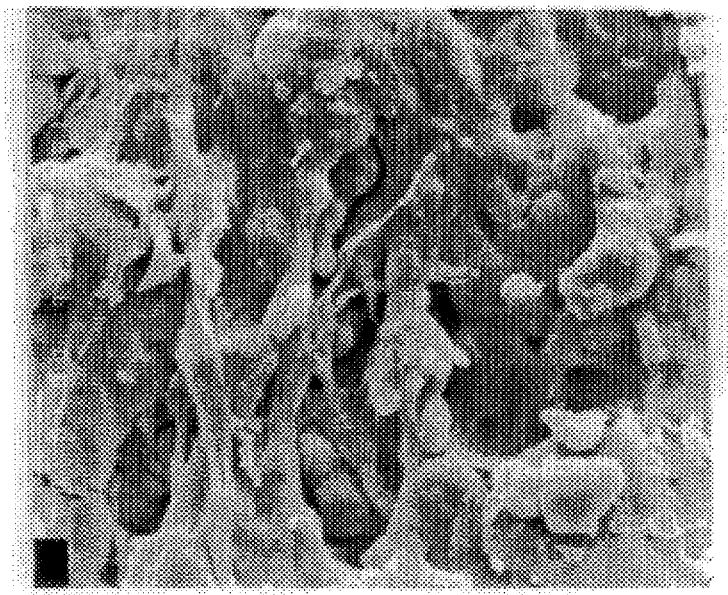
Figure 67:
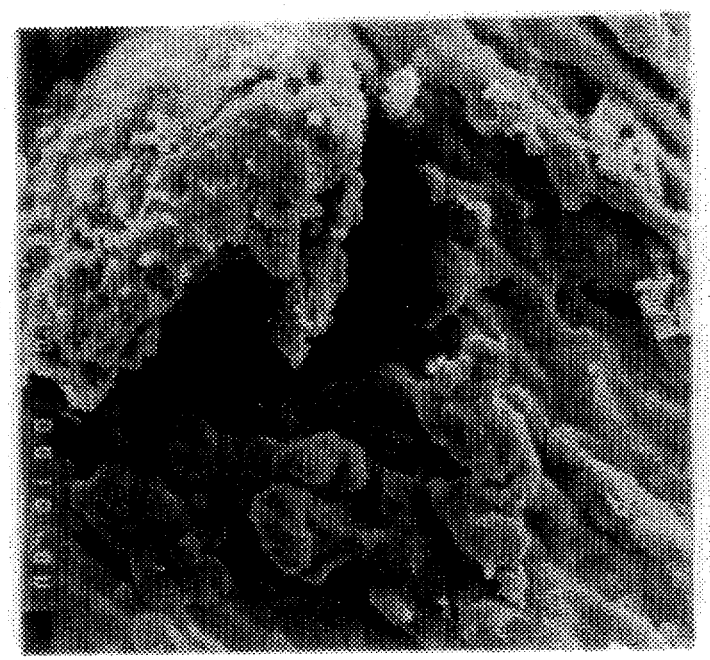
Figure 68:
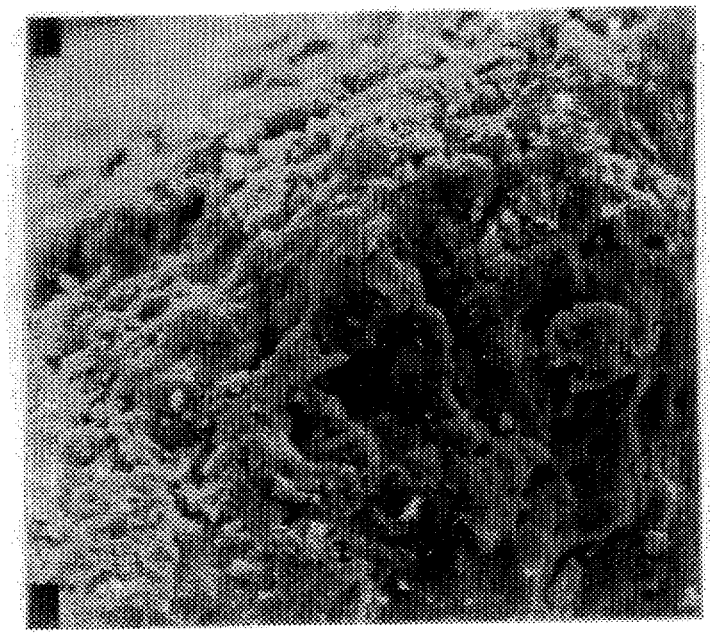

Release rate FIGS. 27 and 23 show release rate independent of testing conditions, while degradation depends on moisture and temperature FIGS. 22 and 24

Effect of the starch modification on the release rate and degradation rate

By selecting the starch modification the release rate of active agent and the degradation rate of the matrix can be varied. This is shown by testing two biodegradable chlorpyrifos formulations given in Table 4.

FIGS. 25, 27, 29, 31, 33 and 35, clearly show that desired release rate of active agent can be obtained by chemical modification of the starch.

FIGS. 26, 28, 30, 32, 34 and 36 show effect of starch modification on matrix degradation.

The processing and extrusion conditions for G01S05 014241 are the same as described above. G01S08 038241 was produced using similar processing temperatures and conditions.

Effect of the incorporation of synthetic polymer (PVC) on the release rate of chlorpyrifos and degradation rate of the matrix The incorporation of synthetic polymers decreases both release rates of the active agent and degradation rate of the matrix.

This is shown on examples of the High Amylose starch based controlled release formulation G01S08 and formulation G01S12 where 5% of the starch is replaced with Corvic 6733 (PVC) as given in Table 5.

TABLE 4

| | | Formulation details | | | | | |
|---|---|---|---|---|---|---|---|
| | | \multicolumn{6}{c}{Composition} | | | | | |
| Formul. No. | Batch No. | Starch | | Glycerol | Water | Attapulgite | Chlorpyrifos |
| | | A948 | HA008 | | | | |
| G01S05 | 014241 | 63.9 | — | 4.0 | 17.3 | 4.5 | 10.3 |
| G01S08 | 038241 | — | 64.2 | 4.0 | 17.0 | 4.5 | 10.3 |

G01S05—Octenylsuccinic anhydride modified High Amylose starch based controlled release formulation.

G01S08—High Amylose starch based controlled release formulation HA008—High Amylose starch (Min. 80% Amylose)

A 948—Octenylsuccinic Anhydride modified High Amylose (HA008) starch.

FIGS. 25–36 show effect of starch modification on the release rate of chlorpyrifos and the degradation rate of the matrix.

TABLE 5

Formulation details

| Formul. No. | Batch No. | Starch HA008 | Glycerol | Water | Attapulgite | Corvic 6733 | Chlorpyrifos |
|---|---|---|---|---|---|---|---|
| G01S08 | 038241 | 64.2 | 4.0 | 17.0 | 4.5 | — | 10.3 |
| G01S12 | 038242 | 60.2 | 4.0 | 16.0 | 4.5 | 5.0 | 10.3 |

FIGS. 37–48 show effect of the incorporation of synthetic polymer (PVC) on the release rate of chlorpyrifos and the degradation rate of the matrix.

FIGS. 37, 39, 41, 43, 45 and 47 show that release rate of active agent can be modified by incorporation of synthetic polymer.

FIGS. 38, 40, 42, 44, 46 and 48 show effect of synthetic polymer incorporation on the degradation rate of the matrix.

Scanning Electron Microscopy Evaluation

Scanning electron microscopy (SEM) technique has been used for evaluating starch and starch-synthetic polymer based controlled release matrixes with active agent (chlorpyrifos) and without it. Formulations used for this trials are given in Table 6.

TABLE 6

Formulation details of the pellets used for SEM trials

| Formul. No. | Batch No. | Starch G 50 | Glycerol | Water | Attapulgite | Corvic 6733 | Chlorpyrifos |
|---|---|---|---|---|---|---|---|
| G01S01 | 344141 | 64.6 | 8.6 | 13.0 | 4.5 | — | 9.3 |
| GBAS01 | 080241 | 71.2 | 9.5 | 14.3 | 5.0 | — | — |
| G01S09 | 029241 | 60.2 | 4.0 | 16.0 | 4.5 | 5.0 | 10.3 |
| GBAS09 | 080249 | 67.1 | 4.5 | 17.8 | 5.0 | 5.6 | — |

G01S01—Controlled release formulation based on Gelose 50 (G 50 High Amylose corn starch) containing active agent.

GBAS01—Controlled release matrix for formulation G01S01, no active agent.

G01S09—Controlled release formulation based on starch Gelose 50 and synthetic polymer (PVC) containing active agent.

GBAS09—Controlled release matrix for formulation G01S09, no active agent.

Extrusion conditions were exactly the same for all formulations, details are given in Table 7.

TABLE 7

Extrusion conditions

| Extrusion Parameters | | Formulation G01S01 | Formulation GBAS01 | Formulation G01S09 | Formulation GBAS09 |
|---|---|---|---|---|---|
| Extruder Barrel Zones Temperatures | Zone 1 | 75/75 | 75/76 | 75/76 | 75/76 |
| | Zone 2 | 77/78 | 77/79 | 77/79 | 77/79 |
| | Zone 3 | 80/80 | 80/81 | 80/81 | 80/82 |
| | Zone 4 | 83/83 | 83/84 | 83/84 | 83/85 |

TABLE 7-continued

Extrusion conditions

| Extrusion Parameters | | Formulation G01S01 | Formulation GBAS01 | Formulation G01S09 | Formulation GBAS09 |
|---|---|---|---|---|---|
| Set/Actual [°C.] | Zone 5 | 86/87 | 86/87 | 86/87 | 86/89 |
| | Zone 6 | 90/91 | 90/91 | 90/91 | 90/92 |
| Die Temperature Set/Actual | [°C.] | 90/90 | 90/91 | 90/91 | 90/91 |
| Extruder Vacuum [-KPa] | Zone 4 | 0 | 0 | 0 | 0 |
| | Zone 5 | 0 | 0 | 0 | 0 |
| | Pressure [psi] | 770 | 790 | 820 | 820 |
| Extruder | Speed [RPM] | 160 | 160 | 160 | 160 |
| | Load [AMPS] | 7 | 8 | 12 | 13 |
| Pelletizer | Puller | 155 | 155 | 155 | 155 |
| | Cutter | 007 | 007 | 007 | 007 |
| Pellet size mm [L × D] | | 2.0 × 1.8 | 2.0 × 1.8 | 2.0 × 1.8 | 2.0 × 1.8 |

The light microscopy and scanning electron microscopy were conducted at the University of Technology Sydney Australia.

Light Microscopy

Light Microscopy (magnification×40) was conducted for all formulations containing active agent and formulation without it.

As shown in the accompanying photographs PH1 and PH2, all the light micrographs of pellets displayed the presence of a coherent structure of the granules. At this level of magnification details of starch structure is not visible.

Scanning Electron Microscopy

The pellets were freeze dried for 48 hours prior to mounting to remove any moisture present. This is to insure than after the pellet has been coated with gold/palladium and introduced into vacuum of the SEM that no moisture could be released that would damage the surface coating of the pellet.

Pellets of samples G01S01, GBAS01, G01S09 and GBAS09, were examined for the presence of residual starch granules.

As indicated in SEM photomicrographs, FIGS. 49–52 the nodular and lumpy structures were clearly and abundantly evident in all samples. See the table below for the details of the photomicrographs.

| FIGURE No | Magnification | Sample No | Description |
|---|---|---|---|
| 53 | 1000 | — | Starch Gelose 50 (G50) granules |
| 54 | 1000 | — | Starch Gelose 50 (G50) |

-continued

| FIGURE No | Magnification | Sample No | Description |
|---|---|---|---|
| | | | granules |
| 55 | 300 | — | PVC granules |
| 56 | 30 | — | PVC granules - particle size distribution |
| 57 | 20 | — | Chlorpyrifos crystals - particle size distribution |
| 58 | 300 | — | Chlorpyrifos crystals |
| 59 | 20 | — | Attapulgite clay - particle size distribution |
| 60 | 300 | — | Attapulgite clay - fine particles |
| 61 | 1000 | 344141 | Lumpy structure of the pellet |
| 62 | 3000 | 344141 | Lumpy Structure of the pellet |
| 63 | 600 | 080241 | Lumpy pellet surface |
| 64 | 1000 | 080241 | Granule cut longitudinally with a scalpel |
| 65 | 1000 | 029241 | PVC fibres on the pellet surface/lumpy pellet structure |
| 66 | 1500 | 029241 | PVC fibres around starch granules |
| 67 | 1000 | 080249 | Machine cut surface of the pellet |
| 68 | 1000 | 080249 | Edge of the pellet |

The size of the globular shapes in the extruded pellets is consistent with the size of the maize starch granules used in the formulation, indicating that the original starch granule structure remains evident in controlled release products produced under the conditions described above. It is evident that no structural change, i.e. no destructurisation of the starch occurred.

Field evaluation

Two formulations G01S05 & G01S09 were evaluated in a bioassay trial against the eastern false wireworm. Formulation G01S905 was also evaluated in a field trial for the residual control of chironomid larvae (bloodworms) in establishing rice crops, Both trials showed excellent performance of starch based control release formulations.

Microorganisms for biological control may be used as active agents in the compositions of the invention.

An example of such microorganisms is *Bacillus thuringiensis* var. kurstake (Bt). This microorganism does not survive in an infectious form in soil. As will be shown in the Example described below, incorporation of Bt into compositions of the invention gives biologically active formulations.

EXAMPLE

Formulations

A series of 9 formulations of Bt technical (as a 10% w/w concentrate) were prepared as per Table 8. The key points on these formulations were:

All contained 50% w/w of the Bt technical

Starch base was Gelose 22 (Starch Australasia)

All formulations contained glycerine (glycerol) as a plasticizer for the starch matrix.

Water levels in the formulations varied from 10% w/w to 18.75% w/w on the prefeed mixture.

Urea was added to some formulations to improve the plasticizing of the starch matrix.

Calcium stearate was added to 2 formulations to improve the extrusion properties of the matrix (to act as an internal lubricant).

Processing Conditions

Extruder temperatures were set at 40° C. for zones 1 through to 6 in the Betol 40L twin screw co-rotating intermeshing extruder. The die temperature (zone 7) was set at 40° C. or 50° C. for the extrusion runs.

Evaluation

The products were evaluated for physical strength and

| Batch No. | Gelose 22 | Water | Glycerine | Urea | Ca Stearate | Bt Technical | | TEMPERATURES Zone 1 | Zone 2 | Zone 3 | Zone 4 | Zone 5 | Zone 6 | Zone 7 (die) | Melt pressure (psi) | Spore count/ gram | Comments |
|---|---|---|---|---|---|---|---|---|---|---|---|---|---|---|---|---|---|
| 041341 | 44.80 | 12.50 | 5.00 | 0.50 | | 50.00 | Set point | 40 | 40 | 40 | 40 | 40 | 40 | 40 | | | Coud not extrude. Hi-pressure trips. |
| | | | | | | | Actual | 40 | 43 | 49 | 48 | 46 | 45 | 44 | | | |
| 042341 | 44.80 | 18.75 | 7.50 | 0.50 | | 50.00 | Set point | 40 | 40 | 40 | 40 | 40 | 40 | 40 | | | Pelletized after extrusion completed. Reasonable cut. |
| | | | | | | | Actual | 40 | 55 | 48 | 47 | 56 | 51 | 45 | | | |
| 042342 | 42.80 | 12.50 | 5.00 | 0.50 | 2.00 | 50.00 | Set point | 40 | 40 | 40 | 40 | 40 | 40 | 40 | | | Coud not extrude. Hi-pressure trips. Worse than 041341. |
| | | | | | | | Actual | | | | | | | | | | |
| 042343 | 42.80 | 18.75 | 7.50 | 0.50 | 2.00 | 50.00 | Set point | 40 | 40 | 40 | 40 | 40 | 40 | 40 | | | Coud not extrude. Hi-pressure trips. |
| | | | | | | | Actual | | | | | | | | | | |
| 043341 | 44.00 | 18.75 | 7.50 | 1.00 | | 50.00 | Set point | 40 | 40 | 40 | 40 | 40 | 40 | 40 | 1100 | 3.0 × 10(8) | Strands very soft. Strands cooled 30 mins. Pelletized without deformation and with consistent length. |
| | | | | | | | Actual | | | | No recording | | | | | | |
| 043342 | 45.00 | 18.75 | 7.50 | | | 50.00 | Set point | 40 | 40 | 40 | 40 | 40 | 40 | 50 | 1000 | 1.8 × 10(7) | Could be pelletized as produced, lacking strand strength. |
| | | | | | | | Actual | 40 | 55 | 49 | 49 | 55 | 52 | 49 | | | |
| 043343 | 40.00 | 13.75 | 12.50 | | | 50.00 | Set point | 40 | 40 | 40 | 40 | 40 | 40 | 50 | | | Die heater failure |
| | | | | | | | Actual | 39 | 40 | 40 | 40 | 42 | 41 | 37 | | | |
| 049341 | 40.00 | 13.75 | 12.50 | | | 50.00 | Set point | 40 | 40 | 40 | 40 | 40 | 40 | 50 | 1100 | 3.0 × 10(8) | Strands soft and insufficient strength to cut hot. |
| | | | | | | | Actual | 40 | 55 | 48 | 49 | 57 | 52 | 52 | | | |
| 050341 | 40.00 | 10.00 | 12.50 | | | 50.00 | Set point | 40 | 40 | 40 | 40 | 40 | 40 | 50 | 1060–1130 | 4.2 × 10(6) | Strand strength slightly better than 049341. But not sufficient to cut hot. |
| | | | | | | | Actual | 40–41 | 58–60 | 50–49 | 51–53 | 60–66 | 54–57 | 50–50 | | | |
| 050342 | 44.50 | 18.75 | 7.50 | 0.50 | | 50.00 | Set point | 40 | 40 | 40 | 40 | 40 | 40 | 50 | 980 | | Strand strength and hardness better than 050341. But still not sufficient. More visible porosity in granules cut cold. |
| | | | | | | | Actual | 41 | 56 | 49 | 49 | 57 | 51 | 50 | | | |

Water contents used in formulation calculations
Bt Technical: 6%
Gelose 22: 12% (assumption based on experience)
Product: 6% (Assumption based on experience - 24 hrs storage in open container @ 30 C.
Extrusion
1 kg. batches
10 kg/hr
single strand die
Spore count Bt Tech - 2 × 10(10)/gram compatibility with the processing equipment as measured by the ability to draw strands and to successfully cut the product in a rotating pelletizer.

Several extruded formulations were tested for the ability of the organism to form spores by measuring the number of viable spores in the formulated (extruded) product.

Results

The results from these trials are summarised in Table 8. The key findings are:

The starch matrix incorporating a biological active ingredient can be successfully extruded to form a uniform starch extruded granule.

The Bt can survive the extrusion temperature required to form a uniform granule leaving sufficient live spores to potentially act in soil against pests. There appears to be some correlation of higher extrusion temperatures with low viable spore number. (see batch No. 050342).

No live spores were found on the outside of the granules. This technique of incorporating Bt into a starch matrix using very low extrusion temperature shows promise for the development of "protected" Bt formulation which may remain active in soil for control of soil pests.

It will be apparent that the biodegradable composition according to the present invention offers the following advantages:

(a) the biodegradable composition provides for the controlled release of an active agent therefrom into an environment over a prolonged period as required;

(b) the biodegradable composition may be tailored to exhibit a variety of release and degradation rates in a range of environments;

(c) as apparent from the Figures, where desired, the active agent can be released at an initially high rate and then at a slower rate as required;

(d) the matrix is biodegradable and over a period of time will break down in an environment.

Further, the use of the biodegradable matrices in compositions according to the invention is advantageous in that they exhibit reduced toxicity behaviour when compared with the toxicity of the active agent used alone or in conventional synthetic polymeric formulations as evident from the following dermal toxicity test carried out with moistened product in accordance with the United States Environmental Protection Agency data generation guidelines.

In this regard, phorate was incorporated in a biodegradable matrix in accordance with the formulation shown below in Table 9:

TABLE 9

| Ingredient | TEST Percentage by Weight |
| --- | --- |
| Gelose 50 | 64.5 |
| Water | 14.4 |
| Glycerol | 10.5 |
| Phorate | 10.6 |

Dermal toxicity tests using this formulation, a conventional synthetic polymer formulation comprising 10% w/w phorate and pure phorate (10% w/w) were performed on male rabbits by securing samples to the skin of the test animals for a period of 24 hours. At the expiry of this period, rabbits were examined for mortality and surviving rabbits observed for 14 days before sacrifice and examination. The $LD_{50}$ values are shown below in Table 10.

TABLE 10

| Composition | $LD_{50}$ Dosage mg per kg body weight |
| --- | --- |
| Formulation of Table 2 | 500–1000 |
| Synthetic polymer formulation comprising 10% w/w phorate | 56–71 |
| Technical grade phorate (10% w/w) | 5.2 |

It will be apparent to those skilled in the art from the teachings headed that the invention may be embodied in other forms without departing from the spirit or scope of the invention described.

We claim:

1. A method for manufacture of a biodegradable matrix shape for use in connection with the controlled release delivery of an agriculturally active agent, said method comprising the steps of:

(a) providing a composition comprising an amylaceous material having an amylose content of at least 50% w/w and water, said water being present in an amount of from about 2 to about 30% w/w, said amylaceous material selected from the group consisting of amylose, waxy maize starch, wheat starch, tapioca starch, pea starch and combinations thereof, (b) heating said composition to a temperature of no more than about 150° C. at a pressure of no more than about 4000 psi to form a uniform hot melt from said composition without destructurising said amylaceous material within said composition, and (c) forming said hot melt into a desired matrix shape, incorporating said agriculturally active agent is incorporated in said composition in steps (a) or (b) or within said matrix shape produced in step (c), optionally incorporating within said composition of steps (a) or (b) a filler in an amount of less than about 95% by weight and a plasticizer in an amount of up to about 20% by weight, and further optionally incorporating a synthetic polymer in an amount of up to about 90% by weight within said composition of steps (a) or (b) or within said matrix shape produced in step (c).

2. A method according to claim 1 wherein said active agent is incorporated into said matrix shape by admixing with said composition in step (a).

3. A method according to claim 1 wherein said active agent is admixed with said hot melt during step (b).

4. A method according to claim 1 wherein the hot melt is formed into said matrix shape by extrusion.

5. A method according to claim 4 wherein the temperature during extrusion is in the range of from 70°–100° C. and the pressure is from 200–500 psi.

6. A method according to claim 1 further comprising subjecting the hot melt to atmospheric or sub-atmospheric pressure immediately prior to or during step (b) to remove water from the hot melt prior to the formation of the matrix shape.

7. A method according to claim 6 further comprising the step of crosslinking the amylaceous material during or after step (b).

8. A method according to claim 1 wherein said amylaceous material is selected from the group consisting of amylaceous ethers, amylaceous esters, and combinations thereof, amylaceous alkyl succinates and starch molecules having synthetic polymeric branches grafted thereon.

9. A method according to claim 8 wherein the amylaceous ether is a hydroxyalkyl derivative or carboxyalkyl derivative.

10. A method according to claim 9 wherein the amylaceous ester is a saturated fatty acid derivative.

11. A method according to claim 9 wherein the amylaceous alkyl succinate is starch octenyl succinate.

12. A method according to claim 1 wherein the composition of step (a) comprises from about 2% to about 20% by weight of water.

13. A method according to claim 12 wherein the composition of step (a) comprises from about 5 to about 15% by weight of water.

14. A method according to claim 1 wherein said synthetic polymer is present in the composition in an amount of less than about 25% by weight.

15. A method according to claim 14 wherein the hot melt is formed into the desired shape by extrusion at a temperature of from 120°–140° C. and a pressure of from 100–1000 psi.

16. A method according to claim 15 wherein in step (b), the matrix shape is co-formed with at least one layer of a synthetic polymer.

17. A method according to claim 16 wherein the matrix shape is co-extruded with the synthetic polymer.

18. A method according to claim 15 wherein the matrix shape from step (b) is coated with a synthetic polymer by way of spraying or brushing.

19. A method according to claim 14 wherein said synthetic polymer is present in the composition in an amount of less than about 15% by weight.

20. A method according to claim 1 wherein the synthetic polymer is selected from the group consisting of low density polyethylene and high density polyethylene, a copolymer of ethylene vinyl acetate, a copolymer of ethylene acrylic acid, polyvinyl chloride, polystyrene, chlorinated polyethylene, a copolymer of ethylene propylene, a copolymer of acrylic acid, polyvinyl acetals, polyamines and urethanes.

21. A method according to claim 1 wherein the composition comprises a filler in an amount of less than about 70% by weight of said composition.

22. A method according to claim 21 wherein said filler is selected from the group consisting of metal salts, clays, carbonaceous material, dextrose, talcs, silicas and ammonium sulphate.

23. A method according to claim 22 wherein said filler is selected from the group consisting of calcium carbonate, calcium sulphate, sodium carbonate, sodium sulphate, barium sulphate, kaolin, bentonite and wood flour.

24. A method according to claim 1 wherein a filler is incorporated into said composition prior to or during step (b).

25. A method according to claim 1 wherein the composition of step (a) or step (b) includes a plasticizer selected from the group consisting of a mono- or polyfunctional alcohol, invert sugar, dioctyl phthalate, chlorinated hydrocarbons, vegetable oil, and combinations thereof.

26. A method according to claim 25 wherein said alcohol is selected from the group consisting of polyethylene glycol, acetyl glycol and glycerol.

27. A method according to claim 25 wherein said vegetable oil is soya bean oil.

28. A method according to claim 1 wherein said active agent is selected from the group consisting of acaricides, insecticides, nematicides, herbicides, fungicides, plant growth regulants, fertilizers, trace nutrients, biological control agents and combinations thereof.

29. A method according to claim 28 wherein said active agent is selected from the group consisting of chlorpyrifos, carbosulfan, carbofuran, phorate, diuron and *Bacillus thuringiensis*.

30. A method according to claim 1 wherein said active agent is blended with the matrix shape from step (c).

31. A method according to claim 30 wherein said active agent is incorporated into said matrix shape by immersion or infusion.

32. A method according to claim 30 further comprising the step of cooling or allowing the matrix shape to cool prior to incorporating said agent herewith.

33. A controlled release biodegradable composition comprising a matrix of an amylaceous material in combination with an agriculturally active agent, said matrix formed by (a) providing a composition comprising an amylaceous material having an amylose content of at least 50% w/w and water, said water being present in an amount of from about 2 to about 30% w/w, said amylaceous material selected from the group consisting of amylose, waxy maize starch, wheat starch, tapioca starch, pea starch and combinations thereof, (b) heating said composition to a temperature of no more than about 150° C. at a pressure of no more than about 4000 psi to form a uniform hot melt from said composition without destructurising said amylaceous material, and (c) forming said hot melt into said matrix, and said agriculturally active agent subject to controlled release and selected from the group consisting of acaricides, insecticides, nematicides, herbicides, fungicides, plant growth regulants, fertilizers, trace nutrients, biological control agents and combinations thereof, said matrix optionally comprising up to about 90% by weight of a synthetic polymer, up to about 20% by weight of a plasticizer and up to about 95% by weight of a filler.

34. A controlled release biodegradable composition according to claim 33 comprising a matrix comprising less than about 15% by weight of a synthetic polymer.

35. A controlled release biodegradable composition according to claim 33 wherein the amylaceous material is selected from the group consisting of amylaceous ethers, amylaceous esters, and combinations thereof; amylaceous alkyl succinates and starch molecules having a synthetic polymer grafted thereon.

36. A controlled release biodegradable composition according to claim 35 wherein the amylaceous ether is a hydroxyalkyl derivative or carboxyalkyl derivative.

37. A controlled release biodegradable composition according to claim 36 wherein said amylaceous ether is a hydroxyethyl, hydroxypropyl, hydroxybutyl or carboxymethyl derivative.

38. A controlled release biodegradable composition according to claim 35 wherein the amylaceous alkyl succinate is starch octenyl succinate.

39. A controlled release biodegradable composition according to claim 35 wherein the amylaceous ester is a saturated fatty acid derivative.

40. A controlled release biodegradable composition according to claim 35 wherein said amylaceous material is crosslinked.

41. A controlled release biodegradable composition according to claim 33 wherein the synthetic polymer is selected from the group consisting of low density polyethylene and high density polyethylene, ethylene vinyl acetate copolymers, ethylene acrylic acid copolymers, polyvinyl chlorides, polystyrenes, chlorinated polyethylenes, ethylene propylene copolymers, acrylic acid copolymers, polyvinyl acetals, polyamines and urethanes.

42. A controlled release biodegradable composition according to claim 33 wherein the matrix is coated with the synthetic polymer.

43. A controlled release biodegradable composition according to claim 33 wherein the active agent is selected from the group consisting of chlorpyrifos, carbosulfan, carbofuran, phorate, diuron and *Bacillus thuringiensis*.

44. A controlled release biodegradable composition according to claim 33 wherein the filler is selected from the group consisting of metal salts, clays, carbonaceous material, dextroses, talcs, silicas and ammonium sulphate in an amount of less than about 70% by weight.

45. A controlled release biodegradable composition according to claim 44 wherein said filler is selected from the group consisting of calcium carbonate, calcium sulphate, sodium carbonate, sodium sulphate, barium sulphate, kaolin, bentonite and wood flour.

46. A controlled release biodegradable composition according to claim 33 having a dermal $LD_{50}$ as measured on rabbits which is greater than the dermal $LD_{50}$ for said active agent as measured on rabbits.

47. A controlled release biodegradable composition as claimed in claim 33 which is adapted for application to a crop growing area.

48. A controlled release biodegradable composition according to claim 33 wherein said composition includes a plasticizer selected from the group consisting of a mono- or polyfunctional alcohol, invert sugar, dioctyl phthalate, chlorinated hydrocarbons, vegetable oil and combinations thereof.

49. A controlled release biodegradable composition according to claim 33 wherein said synthetic polymer is present in an amount of up to about 25% by weight.

* * * * *